United States Patent [19]

Axel et al.

[11] 4,399,216

[45] Aug. 16, 1983

[54] PROCESSES FOR INSERTING DNA INTO EUCARYOTIC CELLS AND FOR PRODUCING PROTEINACEOUS MATERIALS

[75] Inventors: Richard Axel, New York; Michael H. Wigler, Cold Spring Harbor; Saul J. Silverstein, Irvington, all of N.Y.

[73] Assignee: The Trustees of Columbia University, New York, N.Y.

[21] Appl. No.: 124,513

[22] Filed: Feb. 25, 1980

[51] Int. Cl.³ .................. C12N 15/00; C12N 5/00; C12P 21/00; C12Q 1/68; C12Q 1/02; C12Q 1/04

[52] U.S. Cl. .................. 435/6; 435/172; 435/240; 435/317; 435/811; 435/948; 435/29; 435/34; 435/68

[58] Field of Search .......... 435/68, 172, 70, 240, 435/241, 948, 811, 6, 29, 34; 424/85, 177, 178, 180

[56] References Cited

U.S. PATENT DOCUMENTS

3,800,035  3/1974  Goore .................. 435/68
4,195,125  3/1980  Wacker ................ 435/172

FOREIGN PATENT DOCUMENTS

2010847  7/1979  United Kingdom ........ 435/71

OTHER PUBLICATIONS

Kretschmer et al., J. Bacteriology 124, 225–231 (1975).
Wigler, Cell 11, 223–232 (1977).
Mantei et al., Nature 281, 40–46 (1979).
Lai et al., PNAS 77(1), 244–248 (Jan. 1980).
Wigler et al., Cell 16, 777–785 (1979).
Wigler et al., Eucaryotic Gene Regulation Proc. Inc.-UCLA Symposia, R. Axel and T. Maniatis, Editors, Academic Press, 457–475 (1979).
Wigler et al., PNAS 76(3), 1373–1376 (1979).
Wold et al., PNAS 76(11), 5684–5688 (1979).
*The Merck Index*, 8th Edition, Merck & Co., Inc., Rahway, N.J., 568 (1968).
Szybalska et al., PNAS 48, 2026–2034 (1962).
McCutchan et al., Journal National Cancer Institute, 41, 351–356 (1968).
Wigler et al., Cell 14, 725–731 (1978).
Willecke et al., Molec. Gen. Genet., 170, 179–185 (1979).
Graf et al., Somatic Cell Genetics 5, 1031–1044 (1979).
Pellicer et al., Cell 14, 131–141 (1978).
Mercola et al., Science 208, 1033–1035 (May 1980).
Wahl et al., J. Biol. Chem., 254(17), 8679–8689 (Sep. 10, 1979).
Anderson et al., Scientific American, 245(1), Jul. 1981, 106–121.
Fox. C & E News, 35, 36, 42, Sep. 29, 1980.
Marx, Science, 208, 386–387, Apr. 1980.
Begley, Newsweek, 80. Apr. 21, 1980.
Miller et al., PNAS 75(7), 3346–3350 (1978).

*Primary Examiner*—Esther M. Kepplinger
*Attorney, Agent, or Firm*—John P. White

[57] ABSTRACT

The present invention relates to processes for inserting DNA into eucaryotic cells, particularly DNA which includes a gene or genes coding for desired proteinaceous materials for which no selective criteria exist. The insertion of such DNA molecules is accomplished by cotransforming eucaryotic cells with such DNA together with a second DNA which corresponds to a gene coding for a selectable marker.

The invention further relates to processes for inserting into eucaryotic cells a multiplicity of DNA molecules including genes coding for desired proteinaceous materials by cotransformation with the desired genes and with amplifiable genes for a dominant selectable marker in the presence of successively higher amounts of an inhibitor. Alternatively, the insertion of multiple copies of desired genes is accomplished by transformation using DNA molecules formed by ligating a DNA molecule including the desired gene to a DNA molecule which includes an amplifiable gene coding for a dominant selectable phenotype such as a gene associated with resistance to a drug in the presence of successively higher amounts of an agent such as a drug against which the gene confers resistance so that only those eucaryotic cells into which multiple copies of the amplifiable gene have been inserted survive.

73 Claims, 2 Drawing Figures

COTRANSFORMATION OF EUCARYOTIC CELLS
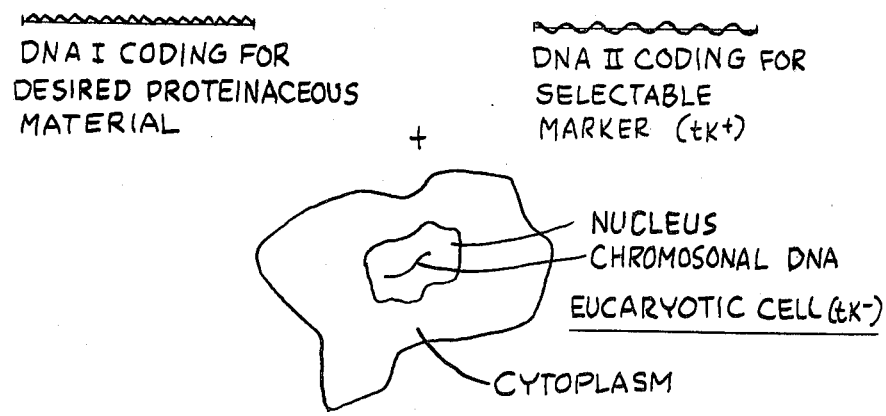
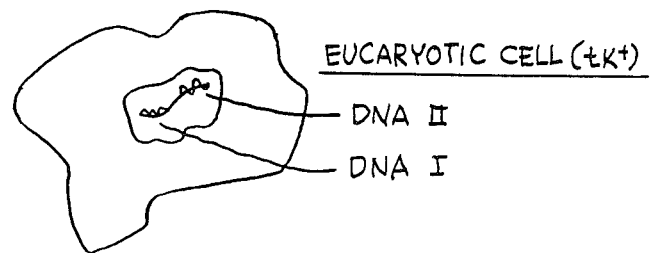
Fig. 1.
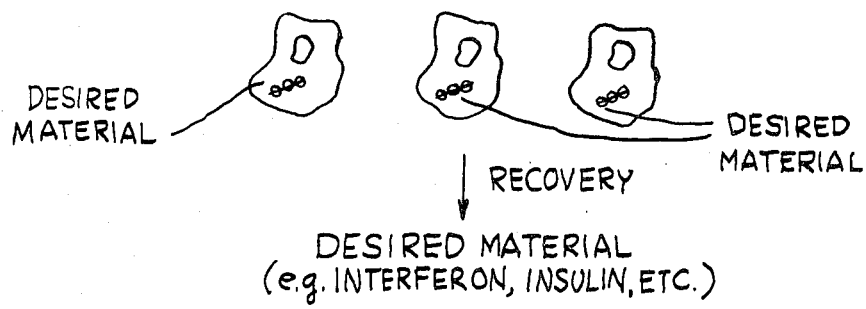

SCHEME FOR THE RESCUE OF BACTERIAL PLASMIDS FROM TRANSFORMED CULTURED CELLS USING DOUBLE SELECTION TECHNIQUES.

PROCESSES FOR INSERTING DNA INTO EUCARYOTIC CELLS AND FOR PRODUCING PROTEINACEOUS MATERIALS

The invention described herein was made in the course of work under grants numbers CA-23767 and CA-76346 from the National Institutes of Health, Department of Health and Human Services.

FIELD OF THE INVENTION

This invention concerns the introduction and expression of genetic informational material, i.e., DNA which includes genes coding for proteinaceous materials and/or genes regulating or otherwise influencing the production thereof, into eucaryotic cells, that is, cells of organisms classified under the Superkingdom Eucaryotes including organisms of the Plant and Animal Kingdoms. Such genetic intervention is commonly referred to as genetic engineering and in certain aspects involves the use of recombinant DNA technology. The invention disclosed is to be distinguished from the introduction of DNA into organisms of the Superkingdom Procaryotes including particularly bacteria. This distinction is based in part upon the basic differences between eucaryotic and procaryotic cells, the former being characterized by true nuclei formed by nuclear envelopes and by meiosis and the latter being characterized by the absence of well-defined nuclei and the absence of meiosis. Moreover, at the genetic level many genes in eucaryotes are split by non-coding sequences which are not continuously colinear, whereas in procaryotes, the genes are continuously colinear.

BACKGROUND OF THE INVENTION

Although advances in the understanding of procaryotic organisms, particularly bacteria, having for the most part proceeded independently of advances in the understanding of eucaryotic organisms, it may be helpful to an appreciation of the present invention to set forth certain developments involving procaryotes.

In 1944, Avery reported the transformation of a procaryotic cell using DNA-mediated transfer of a cellular gene. Avery, O. T., et al., J. Exp. Med. 79: 137–158 (1944). Thereafter, reports of procaryotic transformation occurred in the literature. In 1975, Cohen and others reported results involving first transformation, then cotransformation of the procaryote *Escherichia coli*. Kretschmer, P. J., et al., J. Bacteriology 124: 225–231 (1975). In the experiments reported therein the authors disclosed the cotransformation of procaryotic cells using plasmid DNA, that is, extrachromosomal DNA which occurs naturally in many strains of Enterobacteriacae. In these experiments it was found that particular cells in a $CaCl_2$-treated bacterial population are preferentially competent for tranformation. However, the frequency of transformation and the stability of the transformants obtained was low, possibly because the plasmid is not incorporated into the chromosomal DNA. As a result, cotranformants lost acquired traits after several generations. In addition, these experiments with bacteria required the addition of a gene promoter to the transforming DNA in order to obtain expression.

Meanwhile, experiments with eucaryotic cells proceeded substantially independently of those with procaryotic cells. In 1962, Szybalska, E. H. and Szybalski, W. PNAS 48: 2026 (1962) reported the transformation of mammlian cells but with such low frequency of transformation that it was not possible to distinguish tranformants from cells which had merely undergone spontaneous reversion. Again, as with procaryotic cells, further reports of eucaryotic transformation occurred in the literature, but such results were oftentimes not reproducible by others. In addition, low frequencies of transformation, lack of understanding of the molecular basis for gene expression and the lack of molecular hybridization probes contributed to the lack of progress in this area. As a result, studies on the transformation of eucaryotic cells were essentially restricted to viral genes. Graham, F. L., et al., Cold Spring Harbor Symp. Quant. Biol. 39: 637–650 (1975) and McCutchen, J. H. and Pagano, J. S., Journal National Cancer Institute, 41: 351–357 (1968).

More recently, however, eucaryotic cells, specifically mammalian cells, were transformed with foreign DNA coding for a selectable phenotype. Wigler, M., et al., Cell 11: 223–232 (1977). This work has been extended and has resulted in the present invention wherein it has been discovered inter alia that eucaryotic cells can be cotransformed to yield transformants having foreign DNA integrated into the chromosomal DNA of the eucaryotic cell nucleus. Moreover, it has unexpectedly been discovered that such foreign DNA can be expressed by the cotransformants to generate functional proteins. In addition, by contrast with procaryotic transformants, the foreign DNA is stably expressed through hundreds of generations, a result that may be attributable to integration of the foreign DNA into the chromosomal DNA.

The present invention provides major advances over bacterial systems for future use in the commercial preparation of proteinaceous materials particlarly proteins of eucaryotic origin such as interferon protein, antibodies, insulin, and the like. Such advantages include the ability to use unaltered genes coding for precursors for such proteinaceous materials. After cellular synthesis, the precursor can be further processed or converted within the eucaryotic cell to produce the desired molecules of biological significance. This phenomenon is well known for insulin which is initially produced in the eucaryotic cell as preproinsulin which is then converted to active insulin within the cell by appropriate peptide cleavage. Since procaryotic cells lack the requisite cellular machinery for converting preproinsulin to insulin, the insertion into a procaryotic cell of the eucaryotic gene associated with insulin will result in the production of preproinsulin, not insulin. Although, in the case of insulin, a relatively small and well characterized protein, this difficulty can be overcome by chemical synthesis of the appropriate gene, such an approach is inherently limited by the level of understanding of the amino acid sequence of the desired protein. Thus, for interferon protein, clotting factors, antibodies and uncharacterized enzymes, for which the exact amino acid sequence is not yet known, a procaryotic system will likely not prove satisfactory. By contrast, a eucaryotic system is not associated with such disadvantages since the eucaryotic cell possesses the necessary processing machinery. It is thus one important object of the present invention to provide a process for producing desired proteinaceous materials such as interferon protein, insulin, antibodies and the like which does not require a detailed molecular understanding of amino acid sequence.

In addition to the problem of precursors having additional amino acids which must be removed to produce active protein, important biological materials may be modified by chemical additions after synthesis and cleavage. Thus, for example, human-produced interferon is a glycoprotein containing sugar molecules in addition to protein. If produced in a bacterial cell, the interferon lacks the sugar molecules which are added when interferon is produced in a human cell. Moreover, proteinaceous materials produced within bacteria may include endotoxins which can cause inflammation if the proteinaceous material is administered to a mammal without significant purification. By contrast, interferon produced in a eucaryotic cell would be free of endotoxins.

It is therefore another important object of this invention to provide a process for producing compounds which include both non-proteinaceous and proteinaceous moieties such as glycoproteins which cannot be produced in bacterial cell.

SUMMARY OF THE INVENTION

This invention provides a process for inserting foreign DNA into eucaryotic cells by cotransforming the cells with this foreign DNA and with unlinked DNA which codes for proteinaceous material associated with a selectable phenotype not otherwise expressed by the cell. The cotransformation is carried out in a suitable medium and in the presence of selective conditions permitting survival and/or identification of eucaryotic cells which have acquired the selectable phenotype. The process of this invention is particularly suited for the insertion into eucaryotic cells of DNA which codes for proteinaceous materials which are not associated with a selectable phenotype such as interferon protein, insulin, growth hormones clotting factors, viral antigens, antibodies and certain enzymes.

By use of the cotransformation process of the present invention is it possible to produce eucaryotic cells which synthesize desired proteinaceous and other materials and which can be grown in culture to produce these materials in quantities not obtainable with conventional technology.

In one embodiment of the invention, the cotransformation process can be used to insert multiple copies of genes coding for desired materials into eucaryotic cells. Alternatively, a multiplicity of foreign DNA molecules corresponding to multiple copies of a desired gene can be inserted into eucaryotic cells by transformation with molecules each of which is formed by linking a foreign DNA molecule to a second DNA molecule corresponding to an amplifiable gene for a dominant selectable phenotype not otherwise expressed by the cell. The transformation is then carried out in the presence of successively elevated concentrations of an agent permitting survival and/or identification of eucaryotic cells which have acquired multiple copies of the amplifiable gene. This approach is particularly useful when the dominant selectable phenotype is resistance to a drug which is lethal unless multiple copies of the drug resistant gene are present and the agent is the drug.

By inserting multiple copies of genes coding for desired materials into eucaryotic cells according to either of these approaches it is possible to produce eucaryotic cells which yield desired materials in high concentrations and which can be grown in culture to produce such materials in quantities not obtainable with conventional technology.

BRIEF DESCRIPTION OF THE DRAWINGS

FIG. 1 is a schematic flow diagram illustrating the cotransformation process in accordance with the present invention.

DETAILED DESCRIPTION OF THE INVENTION

Figure 2:
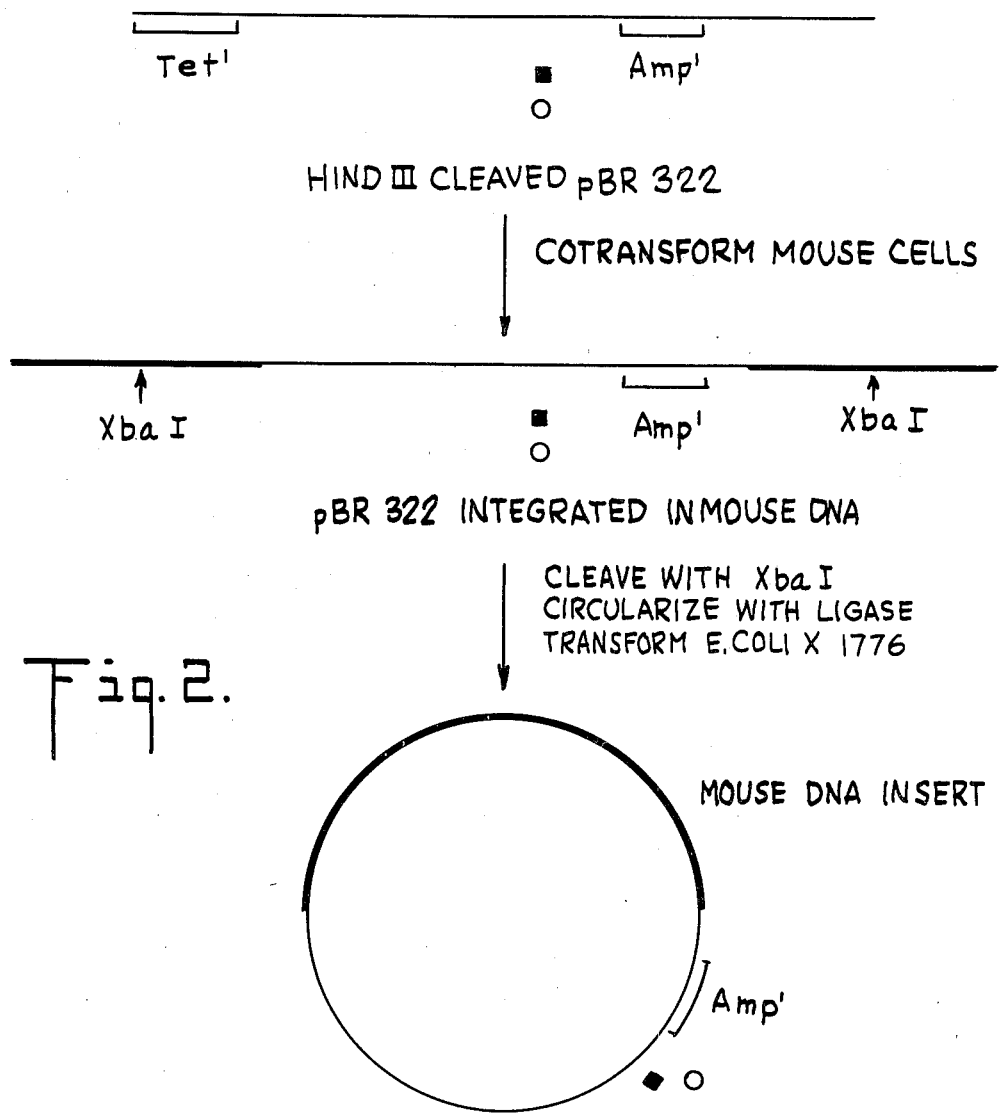
FIG. 2 is a schematic flow diagram illustrating a process for recovering foreign DNA I from cotransformed cultured cells using double selection techniques.

Prior to setting forth the invention, it may be helpful to an understanding thereof to set forth definitions of certain terms to be used hereinafter.

*Transformation* means the process for changing the genotype of a recipient cell mediated by the introduction of purified DNA. Transformation is typically detected by a stable and heritable change in the phenotype of the recipient cell that results from an alteration in either the biochemical or morphological properties of the recipent cell.

*Cotransformation* means the process for carrying out transformations of a recipient cell with more than one different gene. Cotransformation includes both simultaneous and sequential changes in the genotype of a recipient cell mediated by the introduction of DNA corresponding to either unlinked or linked genes.

*Proteinaceous* material means any biopolymer formed from amino acids.

*Genotype* means the genetic constitution of an organism as distinguished from its physical appearance.

*Phenotype* means the observable properties of an organism as produced by the genotype in conjunction with the environment.

*Selectable phenotype* is a phenotype which confers upon an organism ability to exist under conditions which kill off all organisms not possessing the phenotype. Examples include drug resistance or the ability to synthesize some molecule necessary to cell metabolism in a given growth medium. As used herein, selectable phenotypes also include identifiable phenotypes such as the production of materials which pass from or are secreted by the cell and can be detected as new phenotypes either by functional, immunologic or biochemical assays.

*Interferon protein* means the proteinaceous part of the glycoprotein interferon, that is, the portion remaining after removal of the sugar portion. It includes the protein portion of interferon derived from human leukocyte, fibroblast or lymphoblastoid cells.

*Chromosomal DNA* means the DNA normally associated with histone in the form of chromosomes residing in the nucleus of a eucaryotic cell.

*Transcription* means the formation of a RNA chain in accordance with the genetic information contained in the DNA.

*Translation* means the process whereby the genetic information in an mRNA molecule directs the order of specific amino acids during protein synthesis.

In accordance with the present invention, foreign DNA I can be inserted into any eucaryotic cell by cotransforming the cell with DNA I and with unlinked foreign DNA II which includes a gene coding for a selectable phenotype not expressed by the cell unless acquired by transformation. The cotransformation is carried out in a suitable growth medium and in the presence of selective conditions such that the only cells which survive or are otherwise altered are those which have required the selectable phenotype. See FIG. 1.

Although the experiments discussed hereinafter concern cultured eucaryotic cells of mammalian origin such as human blood cells, mouse fibroblast cells, chinese hamster ovary cells and mouse teratocarcinoma cells, it is clear that the process described is generally applicable to all eucaryotic cells including, for example, cells from birds such as chickens, cells from yeast and fungi, and cells from plants including grains and flowers. Therefore, it is to be understood that the invention encompasses all eucaryotic cells even though the invention may ultimately be most useful in cotransforming mammalian cells.

The present invention is especially useful in connection with the insertion into eucaryotic cells of foreign DNA which includes genes which code for proteinaceous materials not associated with selectable phenotypes. Since such proteinaceous materials are characterized by the fact that they are not associated with a selectable phenotype, cells which contain DNA coding therefore cannot be identified except by destruction of the transformed cell and examination of its contents.

Examples of proteinaceus materials, the genes for which may be inserted into and expressed by eucaryotic cells using the cotransformation process include interferon protein, insulin, growth hormones, clotting factors, viral antigens, enzymes and antibodies.

Although in some cases the DNA I and DNA II may not need to be purified to obtain integration and expression, it is oftentimes preferable that the DNAs be purified prior to use in cotransforming cells. Such purification limits the possibility of spurious results due to the presence of contaminants and increases the probability that cotransformed cells can be identified and stably cultured. Also, although not essential, it is sometimes desirable that DNA I and/or DNA II have been obtained by restriction endonuclease cleavage of chromosomal donor DNAs, such as, for example, restriction endonuclease cleavage of eucaryotic chromosomal DNA. Additionally, it is preferable that DNA I and DNA II be treated with calcium phosphate prior to use in cotransforming eucaryotic cells. The procedure for so treating DNA with calcium phosphate is set forth more fully hereinafter. Finally, it is preferable that the foreign DNA I be present during cotransformation in an amount relative to DNA II coding for a selectable phenotype which constitutes an excess of the former, such as an amount in the range from about 1:1 to about 100,000:1.

In a preferred embodiment of the invention, the foreign DNA I and/or the foreign DNA II are attached to bacterial plasmid or phage DNA prior to use in cotransforming eucaryotic cells. In a particularly promising embodiment, foreign DNA I and/or DNA II are attached to phage DNA and then encapsidated in phage particles prior to cotransformation.

Although any DNA II coding for a selectable phenotype would be useful in the cotransformation process of the present invention, the experimental details set forth particularly concern the use of a gene for thymidine kinase obtained from herpes simplex virus and the use of a gene for adenine phosphoribosyl transferase. In addition, a DNA II which includes a gene coding for a selectable phenotype associated with drug resistance, e.g., a mutant dihydrofolate reductase gene which renders cells resistant to methotrexate greatly extends the applicability of the process.

In accordance with a preferred embodiment, the cotransformation involves DNA I which is physically and chemically unlinked to DNA II, and the DNA I is stably integrated into the chromosomal DNA within the nucleus of the cotransformed eucaryotic cell.

Cotransformation in accordance with this invention may be carried out in any suitable medium limited only in that cotransformed cells be capable of survival and/or identification on the medium. Merely by way of example, a suitable medium for mouse fibroblast cells which have aquired the thymidine kinase gene is HAT described more fully hereinafter. Also, the cotransformation is carried out in the presence of selective conditions which permit survival and/or identification of those cells which have acquired the selectable phenotype. Such conditions may include the presence of nutrients, drug or other chemical antagonists, temperature and the like.

Eucaryotic cells cotransformed in accordance with this invention contain foreign DNA I coding for desired materials which can be recovered from the cells using techniques well known in the art. Additionally, the cells can be permitted to transcribe DNA I to form mRNA which in turn is translated to form protein or other desired material which may be recovered, again using well known techniques. Finally, the cells can be grown in culture, harvested and protein or other desired material recovered therefrom.

Although the desired proteinaceous materials identified hereinabove are natural materials, the process can be equally useful in the production of synthetic biopolymers for which synthetic genes are constructed. Thus, the instant invention provides a process for producing novel proteins not yet in existence. Additionally, it provides a process for producing proteins which, although they presently exist, do so in such minute quntities or in such impure form that their isolation and/or identification cannot otherwise be effected. Finally, the invention provides a process for producing partially proteinaceous products such as the glycoproteins and other products, the synthesis of which is genetically directed.

Another aspect of the invention involves processes for inserting multiple copies of genes into eucaryotic cells in order to increase the amount of gene product formed within the cell. One process for inserting a multiplicity of foreign DNA I molecules into a eucaryotic cell comprises cotransforming the cell with multiple DNA I molecules and with multiple, unlinked foreign DNA II molecules corresponding to multiple copies of an amplifiable gene for a dominant selectable phenotype not otherwise expressed by the cell. This cotransformation process is carried out in a suitable medium and in the presence of an agent permitting survival and/or identification of cells which acquire the dominant selectable phenotype. Preferably, this is done in the presence of successively higher concentrations of such an agent so that only those cells acquiring the highest number of amplifiable dominant genes (DNA II) survive and/or are identified. These cells then also contain multiple copies of DNA I. This approach is particularly appropriate for the insertion of multiple copies of amplifiable genes which confer drug resistance upon the cell, e.g., the mutant dihydrofolate reductase gene which renders cells resistant to methotrexate.

Cotransformed eucaryotic cells which have acquired multiple copies of DNA I may then be used to produce increased amounts of the gene product for which DNA I codes in the same manner as described hereinabove.

Alternatively, multiple copies of foreign genes can be generated in and ultimately expressed by eucaryotic cells by transforming the eucaryotic cells with DNA molecules, each of which has been formed by linking a foreign DNA I to a foreign DNA II which corresponds to an amplifiable gene for a dominant selectable phenotype not normally expressed by the eucaryotic cell. The linkage between DNA I and DNA II is preferably in the form of a chemical bond, particularly a bond formed as a result of enzymatic treatment with a ligase. Transformation with such hybrid DNA molecules so formed is then carried out in a suitable growth medium and in the presence of successively elevated concentrations, e.g., amounts ranging from 1:1 to 10,000:1 on a molarity basis, of an agent which permits survival and/or identification of those eucaryotic cells which have acquired a sufficiently high number of copies of the amplifiable gene. Using this approach, eucaryotic cells which have acquired multiple copies of the amplifiable gene for a dominant selectable phenotype not otherwise expressed by the cell survive and/or are identifiable in the presence of elevated concentrations of an agent complementary to the amplifiable gene which would otherwise result in death or inability to identify the cells.

Although various amplifiable genes for dominant selectable phenotypes are useful in the practices of this invention, genes associated with drug resistance, e.g., the gene for dihydrofolate reductase which renders cells resistant to methotrexate, are particularly suitable.

By using either of the two approaches just described, multiple copies of proteinaceous or other desired molecules can be produced within eucaryotic cells. Thus, for example, multiple molecules of interferon protein, insulin, growth hormone, clotting factor, viral antigen or antibody or of interferon per se can be produced by eucaryotic cells, particularly mammalian cells, which have been transformed using hybrid DNA or contransformed using purified DNA which has been treated with calcium phosphate in the manner described hereinafter. Thus, this invention provides a process for producing highly desired, rare and costly proteinaceous and other biological materials in concentrations not obtainable using conventional techniques.

Still another aspect of the present invention involves the preparation of materials normally produced within eucaryotic cells in minute amounts such as glycoprooteins including interferon, which are in part protein but additionally include other chemical species such as sugars, ribonucleic acids, histones and the like. Although the method or methods by which cells synthesize complicated cellular materials such as the glycoproteins are poorly understood, it is anticipated that by using the process of the present invention it will be possible to synthesize such materials in commercially useful quantities. Specifically, it is anticipated that after inserting a gene or genes for the protein portion of a cellular material such as a glycoprotein, which includes a non-protein portion, into a eucaryotic cell of the type which normally produces such material, the cell will not only produce the corresponding proteinaceous material but will utilize already existing cellular mechanisms to process the proteinaceous materials, if and to the extent necessary, and will also add the appropriate non-proteinaceous material to form the complete, biologically active material. Thus, for example, the complete biologically active glyprotein, interferon, could be prepared by first synthesizing interferon protein in the manner described and additionally permitting the cell to produce the non-proteinaceous or sugar portion of interferon and to synthesize or assemble true interferon therefrom. The interferon so prepared could then be recovered using conventional techniques.

In accordance with the present invention and as described more fully hereinafter, eucaryotic cells have been stably transformed with precisely defined procaryotic and eucaryotic genes for which no selective criteria exist. The addition of a purified viral thymidine kinase (tk) gene to mouse cells lacking this enzyme results in the appearance of stable transformants which can be selected by their ability to grow in HAT medium. Since these biochemical transformants might represent a subpopulation of competent cells which are likely to integrate other unlinked genes at frequencies higher than the general population; contransformation experiments were performed with the viral tk gene and bacteriophage $\Phi$X174, plasmid pBR 322 or cloned chromosomal human or rabbit $\beta$-globin gene sequences. Tk transformants were cloned and analyzed for contransfer of additional DNA sequences by blot hybridization. In this manner, mouse cell lines were identified which contain multiple copies of $\Phi$X, pBR 322, or human and rabbit $\beta$-globin sequences. From one to more than 50 cotransformed sequences are integrated into high molecular weight DNA isolated from independent clones. Analysis of subclones demonstrates that the contransformed DNA is stable through many generations in culture. This cotransformation system allows the introduction and stable integration of virtually any defined gene into cultured eucaryotic cells. Ligation to either viral vectors or selectable biochemical markers is not required.

Cotransformation with dominant-acting markers should in principle permit the introduction of virtually any cloned genetic element into wild-type cultured eucaryotic cells. To this end, a dominant-acting, methotrexate resistant, dihydrofolate reducatse gene from CHO A29 cells was transferred to wild-type cultured mouse cells. By demonstrating the presence of CHO DHFR sequences in transformants, definitive evidence for gene transfer was provided. Exposure of these cells to elevated levels of methotrexate results in enhanced resistance to this drug, accompanied by amplification of the newly transferred gene. The mutant DHFR gene, therefore, has been used as a eucaryotic vector, by ligating CHO A29 cell DNA to pBR 322 sequences prior to transformation. Amplification of the DHFR sequences results in amplification of the pBR sequences. The use of this gene as a dominant-acting vector in eucaryotic cells will expand the repetoire of potentially transformable cells, no longer restricting these sort of studies to available mutants.

Using the techniques described, the cloned chromosomal rabbit $\beta$-globin gene has been introduced into mouse fibroblasts by DNA-mediated gene transfer. The cotransformed mouse fibroblast containing this gene provides a unique opportunity to study the expression and subsequent processing of these sequences in a heterologous host. Solution hybridization experiments in concert with RNA blotting techniques indicate that in at least one transformed cell line rabbit globin sequences are expressed in the cytoplasm as a polyadenylated 9S species. These 9S sequences result from perfect splicing and removal of the two intervening sequences. These results therefor suggest that nonerythroid cells from heterologous species contain the enzymes necessary to correctly process the intervening sequences of a rabbit gene whose expression is usually restricted to erythroid cells. Surprisingly, however, 45 nucleotides present at the 5' terminus of mature rabbit mRNA are absent from the globin mRNA sequence detected in the cytoplasm of the transformants examine. These studies indicate the potential value of cotransformation systems in the analysis of eucaryotic gene expression. The introduction of wild type genes along with native and in vitro constructed mutant genes into cultured cells provides an assay for the functional significance of sequence organization.

Recombinant DNA technology has facilitated the isolation of several higher eucaryotic genes for which hybridization probes are available. Genes expressed at exceedingly low levels, with mRNA transcripts present at from one to 20 copies per cell, such as those genes coding for essential metabolic functions, cannot be simply isolated by conventional techniques involving construction of cDNA clones and the ultimate screening of recombinant libraries. An alternative approach for the isolation of such rarely expressed genes has therefore been developed utilizing transformation in concert with a procedure known as plasmid rescue. This schema which is currently underway in the laboratory is outlined below. The aprt gene of the chicken is not cleaved by the enzyme, Hin III or Xba, and transformation of aprt⁻mouse cells with cellular DNA digested with these enzymes results in the generation of aprt⁺clonies which express the chicken aprt genes. Ligation of Hin III-cleaved chicken DNA with Hin III-cleaved plasmid pBR 322 results in the formation of hybrid DNA molecules in which the aprt gene is now adjacent to plasmid sequences. Transformation of aprt⁻cells is now performed with this DNA. Transformants should contain the aprt gene convalently linked to pBR 322 with this entire complex integrated into high molecular weight DNA in the mouse cell. This initial cellular transformation serves to remove the chicken aprt gene from the vast majority of other chick sequences. This transformed cell DNA is now treated with an enzyme, Xba I, which does not cleave either pBR 322 or the aprt gene. The resultant fragments are then circularized with ligase. One such fragment should contain the aprt gene covalently linked to pBR 322 sequences coding for an origin of replication and the ampicillin resistant marker. Transformation of a bacterium such as E. coli with these circular markers selects for plasmid sequences from eucaryotic DNA which are now linked to chicken aprt sequences. This double selection technique should permit the isolation of genes expressed at low levels in eucaryotic cells for which hybridization probes are not readily obtained.

In order to assist in a better understanding of the present invention, the results of various experiments are now set forth.

EXPERIMENTAL DETAILS

FIRST SERIES OF EXPERIMENTS

The identificaton and isolation of cells transformed with genes which do not code for selectable markers is problematic since current transformation procedures are highly inefficient. Thus, experiments were undertaken to determine the feasibility of cotransforming cells with two physically unlinked genes. In these experiments it was determined that cotransformed cells could be identified and isolated when one of the genes codes for a selectable marker. Viral thymidine kinase gene was used as a selectable marker to isolate mouse cell lines which contain the tk gene along with either bacteriphage ΦX 174, plasmid pBR 322 or cloned rabbit β-globin gene sequences stably integrated into cellular DNA. The results of these experiments are also set forth in Wigler, M., et al., Cell 16; 777–785 (1979) and Wold, B. et al., Proc. Nat'l. Acad. Sci. 76: 5684–5688 (1979) are as follows:

EXPERIMENTAL DESIGN

The addition of the purified thymidine kinase (tk) gene from herpes simplex virus to mutant mouse cells lacking tk results in the appearance of stable transformants expressing the viral gene which can be selected by their ability to grow in HAT. Maitland, N. J. and McDougall J. K. Cell, 11: 233–241 (1977); Wigler, M. et al., Cell 11: 223–232 (1977). The obtain cotransformants, cultures are exposed to the tk gene in the presence of an excess of a well-defined DNA sequence for which hybridization probes are available. Tk transformants are isolated and scored for the cotransfer of additional DNA sequences by molecular hybridization.

Cotransformation of Mouse Cells with Φ174 DNA

ΦX174 DNA was initially used in cotransformation experiments with the tk gene as the selectable marker. ΦX replicative form DNA was cleaved with Pst 1, which recognizes a single site in the circular genome. Sanger, F. et al., Nature 265: 687–695 (1977). 500 pg of the purified tk gene were mixed with 1–10 μg of Pst-cleaved ΦX replicative form DNA. This DNA was then added to mouse Ltk⁻cells using the transformation conditions described under Methods and Materials hereinafter. After 2 weeks in selective medium (HAT), tk⁺transformants were observed at a frequency of one colony per 10 cells per 20 pg of purified gene. Clones were picked and grown to mass culture.

It was then asked whether tk⁺transformants also contained ΦX DNA sequences. High molecular weight DNA from the transformants was cleaved with the restriction endonuclease Eco RI, which recognizes no sites in the ΦX genome. The DNA was fractionated by agarose gel electrophoresis and transferred to nitrocellulose filters, and these filters were then annealed with nick-translated $^{32}$P-ΦX DNA (blot hybridization). Southern, R. M., J. Mol. Biol. 98: 503–517 (1975); Botchan, M., et al., Cell 9: 269–287 (1976); Pellicer, A., et al. Cell 14: 133–141 (1978). These annealing experiments demonstrate that six of the seven transformants had acquired bacteriophage sequences. Since the ΦX genome is not cut by the enzyme Eco RI, the number of bands observed reflects the minimum number of eucaryotic DNA fragments containing information homologous to ΦX. The clones contain variable amounts of ΦX sequences. Clones ΦX1 and ΦX2 reveal a single annealing fragment which is smaller than the ΦX genome. In these clones, therefore, only a portion of the transforming sequences persist. There was also observed a tk⁺transformant (clone 101 X3) with no detectable ΦX sequences. Clones ΦX4, 5, 6, and 7 reveal numerous high molecular weight bands which are too closely spaced to count, indicating that these clones contain multiple ΦX-specific fragments. These experiments demonstrate cotransformation of cultured mammalian cells with the viral tk gene and ΦX DNA.

Selection is Necessary to identify ΦX Transformants

It was next asked whether transformants with ΦX DNA was restricted to the population of tk+ cells or whether a significant proportion of the original culture now contained ΦX sequences. Cultures were exposed to a mixtures of the tk gene and ΦX DNA in a molar ratio of 1:2000 or 1:20,000. Half of the cultures were plated under selective conditions, while the other half were plated in neutral media at low density to facilitate cloning. Both selected (tk+) and unselected (tk−) colonies were picked, grown into mass culture and scored for the presence of ΦX sequences. In this series of experiments, eight of the nine tk+selected colonies contained phage information. As in the previous experiments, the clones contained varying amounts of ΦX DNA. In contrast, none of fifteen clones picked at random from neutral medium contained any ΦX information. Thus, the addition of a selectable marker facilitates the identificaton of those cells which contain ΦX DNA.

ΦX Sequences are Integrated into Cellular DNA

Cleavage of DNA from ΦX transformants with Eco RI generates a series of fragments which contain ΦX DNA sequences. These fragments may reflect multiple integration events. Alternatively, these fragments could result from tandem arrays of complete or partial ΦX sequences which are not integrated into cellular DNA. To distinguish between these possibilities, transformed cell DNA was cut with BAM HI or Eco RI, neither of which cleaves the ΦX genome. If the ΦX DNA sequences were not integrated, neither of these enzymes would cleave the ΦX fragments. If the ΦX DNA sequences were not integrated, neither of these enzymes would cleave the ΦX fragments. Identical patterns would be generated from undigested DNA and from DNA cleaved with either of these enzymes. If the sequences are integrated, then BAM HI and Eco RI should recognize different sites in the flanking cellular DNA and generate unique restriction patterns. DNA from clones ΦX4 and ΦX5 was cleaved with BAM III or Eco RI and analyzed by Southern hybridization. In each instance, the annealing pattern with Eco RI fragments differed from that observed with the BAM HI fragments. Furthermore, the profile obtained with undigested DNA reveals annealing only in very high molecular weight regions with no discrete fragments observed. Similar observations were made on clone ΦX1. Thus, the most of the ΦX sequences in these three clones are integrated into cellular DNA.

Intracellular Localization of the ΦX Sequences

The location of ΦX sequences in transformed cells was determined by subcellular fractionation. Nuclear and cytoplasmic fractions was prepared, and the ΦX DNA sequence content of each was assayed by blot hybridization. The data indicate that 95% of the ΦX sequences are located in the nucleus. High and low molecular weight nuclear DNA was prepared by Hirt fractionation. Hirt, B. J., Mol. Biol. 26: 365–369 (1967). Hybridization with DNA from these two fractions indicates that more than 95% of the ΦX informaton co-purifies with the high molecular weight DNA fraction. The small amount of hybridization observed in the supernatant fraction reveals a profile identical to that of the high molecular weight DNA, suggesting contamination of this fraction with high molecular weight DNA.

Extent of Sequence Representation of the ΦX Genome

The annealing profiles of DNA from transformed clones digested with enzymes that do not cleave the ΦX genome provide evidence that integration of ΦX sequences has occured and allow us to estimate the number of ΦX sequences integrated. Annealing profiles of DNA from transformed clones digested with enzymes which cleave within the ΦX genome allow us to determine what proportion of the genome is present and how these sequences are arranged following integration. Cleavage of ΦX with the enzyme Hpa I generates three fragments for each integration event: two "internal" fragments of 3.7 and 1.3 kb which together comprise 90% of the ΦX genome, and one "bridge" fragment of 0.5 kb which spans the Pst I cleavage site. In the annealing profile observed when clone ΦX4 is digested with Hpa I, two intense bands are observed at 3.7 and 1.3 kb. A less intense series of bands of higher molecular weight is also observed, some of which probably represent ΦX sequences adjacent to cellular DNA. These results indicate that at least 90% of the ΦX genome is present in these cells. It is worth noting that the internal 1.3 kb Hpa I fragment is bounded by an Hpa I site only 30 bp from the Pst I cleavage site. Comparison of the intensities of the internal bands with known quantities of Hpa I-cleaved ΦX DNA suggests that this clone contains approximately 100 copies of the ΦX genome. The annealing pattern of clone 5 DNA cleaved with Hpa I is more complex. If internal fragments are present, they are markedly reduced in intensity; instead, multiple bands of varying molecular weight are observed. The 0.5 kb Hpa I fragment which bridges the Pst I cleavage site is not observed for either clone ΦX4 or clone ΦX5.

A similar analysis of clone ΦX4 and ΦX5 was performed with the enzyme Hpa II. This enzyme cleaves the ΦX genome five times, thus generating four "internal" fragments of 1.7, 0.5, 0.5 and 0.2 kb, and a 2.6 kb "bridge" fragment which spans the Pst I cleavage site. The annealing patterns for Hpa II-cleaved DNA from ΦX clones 4 and 5 each show an intense 1.7 kb band, consistent with the retention of at least two internal Hpa II sites. The 0.5 kb internal fragments can also be observed, but they are not shown on this gel. Many additional fragments, mostly of high molecular weight, are also present in each clone. These presumably reflect the multiple integration sites of ΦX DNA in the cellular genome. The 2.6 kb fragment bridging the Pst I cleavage site, however, is absent from clone ΦX4. Reduced amounts of annealing fragments which co-migrate with the 2.6 kb Hpa II bridge fragment are observed in clone ΦX5. Similar observations were made in experiments with the enzyme Hae III. The annealing pattern of Hae III-digested DNA from these clones was determined. In accord with previous data, the 0.87 kb Hae III bridge fragment spanning the Pst site is absent or present in reduced amount in transformed cell DNA. Thus, in general, "internal" fragments of ΦX are found in these transformants, while "bridge" fragments which span the Pst I cleavage site are reduced or absent.

Stability of the Transformed Genotype

Previous observations on the transfer of selectable biochemical markers indicate that the transformed phenotype remains stable for hundreds of generations if cells are maintained under selective pressure. If maintained in neutral medium, the transformed phenotype is lost at frequencies which range from 0.1 to as high as 30% per generation. Wigler, M., et al., Cell 11; 223–232 (1977); Wigler, M. et al., PNAS 76: 5684–5688 (1979). The use of transformation to study the expression of foreign genes depends upon the stability of the transformed genotype. This is an important consideration with genes for which no selective criteria are available. It was assumed that the presence of ΦX DNA in transformants confers no selective advantage on the recipient cell. Therefore, the stability of the ΦX genotype was examined in the descendants of two clones after numerous generations in culture. Clone ΦX4 and ΦX5, both containing multiple-copies of ΦX DNA, were subcloned and six independent subclones from each clone were picked and grown into mass culture. DNA from each of these subclones from each original clone were picked and grown into mass culture. DNA from each of these subclones was then digested with either Eco RI or Hpa I, and the annealing profiles of ΦX-containing fragments were compared with those of the original parental clone. The annealing pattern observed for four of the six ΦX4 subclones is virtually identical to that of the parent. In two subclones, an additional Eco RI fragment appeared which is of identical molecular weight in both. This may have resulted from genotypic heterogeneity in the parental clone prior to subcloning. The patterns obtained for the subclones of ΦX5 are again virtually identical to the parental annealing profile. These data indicate that ΦX DNA is maintained within the ten subclones examined for numerous generations without significant loss or translocation or information.

Integration of pBR322 into Mouse Cells

The observations in cotransformation have been extended to the EK2-approved bacterial vector, plasmid pBR322. pBR322 linearized with BAM HI was mixed with the purified viral tk gene in a molar ratio of 1000:1. Tk+ transformants were selected and scored for the presence of pBR322 sequences. Cleavage of BAM HI linearized pBR322 DNA with Bgl I generates two internal fragments of 2.4 and 0.3 kb. The sequence content of the pBR322 transformants was determined by digestion of transformed cell DNA with Bgl I followed by annealing with $^{32}$p-labeled plasmid DNA. Four of five clones screened contained the 2.4 kb internal fragment. The 0.3 kb fragment would not be detected on these gels. From the intensity of the 2.4 kb band in comparison with controls, we conclude that multiple copies of this fragment are present in these transformants. Other bands are observed which presumably represent the segments of pBR322 attached to cellular DNA.

Transformation of Mouse Cells with the Rabbit β-Globin Gene

Transformation with purified eucaryotic genes may provide a means for studying the expression of cloned genes in a heterologous host. Cotransformation experiments were therefore performed with the rabbit β major globin gene which was isolated from a cloned library of rabbit chromosomal DNA (Maniatis, T., et al., Cell 15: 687–701 (1978). One β-globin clone designated RβG-1 consists of a 15 kb rabbit DNA fragment carried on the bacteriophage cloning vector Charon 4a. Intact DNA from this clone (RβG-1) was mixed with the viral tk DNA at a molar ratio of 100:1, and tk+ transformants were isolated and examined for the presence of rabbit globin sequences. Cleavage of RβG-1 with the enzyme Kpn I generates a 4.7 kb fragment which contains the entire rabbit β-globin gene. This fragment was purified by gel electrophoresis and nick-translated to generate a probe for subsequent annealing experiments. The β-globin genes of mouse and rabbit are partially homologous, although we do not observe annealing of the rabbit β-globin probe with Kpn-cleaved mouse DNA under our experimental conditions. In contrast, cleavage of rabbit liver DNA with Kpn I generates the expected 4.7 kb globin band. Cleavage of transformed cell DNA with the enzyme Kpn I generates a 4.7 kb fragment containing globin-specific information in six of the eight tk+ transformants examined. In two of the clones, additional rabbit globin bands are observed which probably result from the loss of at least one of the Kpn sites during transformation. The number of rabbit globin genes integrated in these transformants is variable. In comparison with controls, some clones contain a single copy of the gene, while others contain multiple copies of this heterologous gene. These results demonstrate that cloned eucaryotic genes can be introduced into cultured mammalian cells by cotransformation.

TRANSFORMATION COMPETENCE IS NOT STABLY INHERITED

Our data suggest the existenc of a subpopulation of transformation-competent cells within the total cell population. If competence is a stably inherited trait, then cells selected for transformation should be better recipients in subsequent gene transfer experiments than their parental cells. Two results indicate that as in procaryotes, competence is not stably heritable. In the first series of experiments, a double mutant, Ltk aprt$^-$ (deficient in both tk and aprt), was transformed to either the tk+ aprt$^-$ or the tk$^-$ aprt+ phenotype using cellular DNA as donor. Wigler, M. et al., Cell 14: 725–731 (1978); Wigler, M. et al., PNAS 76: 5684–5688 (1979). These clones were then transformed to the tk+ aprt+ phenotype. The frequency of the second trnasformation was not significantly higher than the first. In another series of experiments, clones ΦX4 and ΦX5 were used as recipients for the transfer of a mutant folate reductase gene which renders recipient cells resistant to methotrexate (mtx). The cell line A29 Mtx$^{RIII}$ contains a mutation in the structural gene for dihydrofolate reductase, reducing the affinity of this enzyme for methotrexate. Flintoff, W. F. et al., Somatic Cell Genetic 2: 245–261 (1976). Genomic DNA from this line was used to transform clones ΦX4 and ΦX5 and Ltk$^-$ cells. The frequency of transformation to mtx resistance for the ΦX clones was identical to that observed with the parental Ltk$^-$ cells. It is therefore concluded that competence is not a stably heritable trait and may be a transient property of cells.

DISCUSSION

In these studies, we have stably transformed mammalian cells with precisely defined procaryotic and eucaryotic genes for which no selective criteria exist. Our chosen design derives from studies of tramsformation in bacteria which indicate that a small but selectable subpopulation of cells is competent in transformation. Thomas, R. Biochim. Biophys. Acta 18: 467–481 (1955); Hotchkiss, R. PNAS 40: 49–55 (1959); Thomasz, A. and Hotchkiss R. PNAS 51: 480–487 (1964); Spizizen, J. et al., Ann Rev. Microbiol. 20: 371–400 (1966). If this is also true for animal cells, then biochemical transformants will represent a subpopulation of competent cells which are likely to integrate other unlinked genes at frequencies higher than the general population. Thus, to identify transformants containing genes which provide no selectable trait, cultures were cotransformed with a physically unlinked gene which provided a selectable marker. This cotransformation system should allow the introduction and stable integration of virtually any defined gene into cultured cells. Ligation to either viral vectors or selectable biochemical markers is not required.

Cotransformation experiments were performed using the HSV tk gene as the selectable biochemical marker. The addition of this purified tk gene to mouse cells lacking thymidine kinase results in the appearance of stable transformants which can be selected by their ability to grow in HAT. $Tk^+$ transformants were cloned and analyzed by blot hybridization for cotransfer of additional DNA sequences. In this manner, we have constructed mouse cell lines which contain multiple copies of ΦX, pBR322 an ribbit β-globin gene sequences.

The suggestion that these observations could result from contaminating procaryotic cells in our cultures is highly improbable. At least one of the rabbit β-globin mouse transformants expresses polyadenylated rabbit β-globin RNA sequences as a discrete 9S cytoplasmic species. The elaborate processing events required to generate 9S globin RNA correctly are unlikely to occur in procaryotes.

The ΦX cotransformants were studied in greatest detail. The frequency of cotransformation is high: 14 of 16 $tk^+$ transformants contain ΦX sequences. The ΦX sequences are integrated into high molecular weight nuclear DNA. The number of integration events varies from one to more than fifty in independent clones. The extent of the bacteriophage genome present within a given transformant is also variable; while some clones have lost up to half the genome, other clones contain over 90% of the ΦX sequences. Analysis of subclones demonstrates that the ΦX genotype is stable through many generations in culture. Similar conclusions are emerging from the characterization of the pBR322 and globin gene cotransformants.

Hybridization analysis of restriction endonuclease-cleaved transformed cell DNA allows one to make some preliminary statements on the nature of the integration intermediate. Only two ΦX clones have been examined in detail. In both clones, the donor DNA was Pst I-linearized ΦX DNA. Attempts were made to distinguish between the integration of a linear or circular intermediate. If either precise circularization or the formation of linear concatamers had occurred at the Psl I cleavage site, and if integration occurred at random points along this DNA, one would expect cleavage maps of transformed cell DNA to mirror the circular ΦX map. The bridge fragment, however, is not observed or is present in reduced amounts in digests of transformed cell DNA with three different restriction endonucleases. The fragments observed are in accord with a model in which ΦX DNA integrates as a linear molecule. Alternatively, it is possible that intramolecular recombination of ΦX DNA occurs, resulting in circularization with deletions at the Pst termini. Lai, C. J. and Nathans, D. Cold Spring Harbor Symp. Quant. Biol. 39: 53–60 (1974). Random integration of this circular molecule would generate a restriction map similar to that observed for clones ΦX4 and ΦX5. Other more complex models of events occurring before, during or after integration can also be considered. Although variable amounts of DNA may be deleted from termini during transformation, most copies of integrated ΦX sequences in clone ΦX4 retain the Hpa I site, which is only 30 bp from the Pst I cleavage site. Whatever the mode of integration, it appears that cells can be stably transformed with long stretches of donor DNA. Transformants have been observed containing continuous stretches of donor DNA 50 kb long.

There have been attempts to identify cells transformed with ΦX sequences in the absence of selective pressure. Cultures were exposed to ΦX and tk DNA and cells were cloned under nonselective conditions. ΦX sequences were absent from all fifteen clones picked. In contrast, 14 of 16 clones selected for the $tk^+$ phenotype contained ΦX DNA. The simplest interpretation is that a subpopulation of cells within the culture is competent in the uptake and integration of DNA. In this subpopulation of cells, two physically unlinked genes can be introduced into the same cell with high frequency. At present one can only speculate on the biological basis of competence. Competent cells may be genetic variants within the culture; however, these studies indicate that the competent phenotype is not stably inherited. If one can extrapolate from studies in procaryotes, the phenomenon of competence is likely to be a complex and transient property reflecting the metabolic state of the cell.

Cotransformants contain at least one copy of the tk gene and variable amounts of ΦX DNA. Although transformation was performed with ΦX and tk sequences at a molar ratio of 1000:1, the sequence ratio observed in the transformants never exceeded 100:1. There may be an upper limit to the number of integration events that a cell can tolerate, beyond which lethal mutations occur. Alternatively, it is possible that the efficiency of transformation may depend upon the nature of the transforming fragment. The tk gene may therefor represent a more efficient transforming agent than phage DNA.

In other studies there has been demonstrated the cotransfer of plasmid pBR322 DNA into $Ltk^-$ $aprt^-$ cells using $aprt^+$ cellular DNA as donor and aprt as selectable marker. Furthermore, the use of dominant acting mutant genes which can confer drug resistance will extend the host range for cotransformation to virtually any cultured cell.

The stable transfer of ΦX DNA sequences to mammalian cells serves as a model system for the introduction of defined genes for which no selective criteria exist. The tk cotransformation system has been used to transform cells with the bacterial plasmid pBR322 and the cloned rabbit β-globin gene. Experiments which indicate that several of the pBR transformants contain an uninterrupted sequence which includes the replicative origin and the gene coding for ampicillin resistance (β-lactamase), suggest that DNA from pBR transformants may transfer ampicillin resistance to E. coli. Although preliminary, these studies indicate the potential value of cotransformation in the analysis of eucaryotic gene expression.

SECOND SERIES OF EXPERIMENTS

Cotransformed mouse fibroblasts containing the rabbit β-globin gene provide an opportunity to study the expression and subsequent processing of these sequences in a heterologous host. In these experiments, we demonstrate the expression of the transformed rabbit β-globin gene generating a discrete polyadenylated 9S species of globin RNA. This RNA results from correct processing of both intervening sequences, but lacks approximately 48 nucleotides present at the 5' terminus of mature rabbit β-globin mRNA.

Transformation of Mouse Cells with the Rabbit β-Globin Gene

We have performed cotransformation experiments with the chromosomal adult rabbit β-globin gene, using the purified herpes virus tk gene as a biochemical marker. The addition of the tk gene to mutant Ltk− mouse fibroblasts results in the appearance of stable transformants that can be selected by their ability to grow in hypoxanthine/aminopterin/thymidine (HAT) medium. Cells were cotransformed with a 62-globin gene clone designated RβG1, which consists of a 15.5-kbp insert of rabbit DNA carried in the bacteriophage λcloning vector Charon 4A. The purified tk gene was mixed with a 100-fold molar excess of intact recombinant DNA from clone RβG1. This DNA was then exposed to mouse Ltk− cells under transformation conditions described herein under Methods and Materials. After 2 weeks in selective medium, tk+ transformants were observed at a frequency of one colony per $10^6$ cells per 20 pg of tk gene. Clones were picked and grown into mass culture.

It was then asked if the tk+ transformants also contain rabbit β-globin sequences. High molecular weight DNA from eight tranformants was cleaved with the restriction endonuclease Knp I. The DNA was fractionated by agarose gel electrophoresis and transferred to nitrocellulose filters, and these filters were then annealed with nicktranslated globin [$^{32}$P] DNA blot hybridization. Southern, E. M., J. Mol. Biol. 98: 503–517 (1975). Cleavage of this recombinant phage with the enzyme Kpn I generates a 4.7-kpb fragment that contains the entire adult β-globin gene, along with 1.4 kbp of 5' flanking information and 2.0 kbp of 3' flanking information. This fragment was purified by gel electrophoresis and nick translated to generate a hybridization probe. Blot hybridization experiments showed that the 4.7-kbp Kpn I fragment containing the globin gene was present in the DNA of six of the eight tk+ transformants. In three of the clones additional rabbit globin bands were observed, which probably resulted from the loss of at least one of the Kpn I sites during transformation. The number of rabbit globin genes integrated in these transformants was variable: some clones contained a single copy of the gene whereas other contained up to 20 copies of the heterologous gene. It should be noted that the β-globin genes of mouse and rabbit are partially homologous. However, we do not observe hybridization of the rabbit β-globin probe to Kpn-cleaved mouse DNA, presumably because Kpn cleavage of mouse DNA leaves the β-gene cluster in exceedingly high molecular weight fragments not readily detected in these experiments. These results demonstrate the introduction of the cloned chromosomal rabbit β-globin transfer.

RABBIT β-GLOBIN SEQUENCES ARE TRANSCRIBED IN MOUSE TRANSFORMANTS

The cotransformation sysem we have developed may provide a functional assay for cloned eucaryotic genes if these genes are expressed in the heterologous recipient cell. Six transformed cell clothes were therefor analyzed for the presence of rabbit β-globin RNA sequences. In initial experiments, solution hybridization reactions were performed to determine the cellular concentration of rabbit globin transcripts in our transformants. A radioactive cDNA copy of purified rabbit α- and β-globin mRNA was annealed with the vast excess of cellular RNA. Because homology exists between the mouse and rabbit globin sequences, it was necessary to determine experimental conditions such that the rabbit globin cDNAs did not form stable hybrids with mouse globin mRNA but did react completely with homologous rabbit sequences. At 75° C. in the presence of 0.4 M NaCl, over 80% hybridization was observed with the rabbit globin mRNA, whereas the heterologous reaction with purified mouse globin mRNA did not exceed 10% hybridization. The $R_0t_{1/2}$ of the homologous hybridization reaction was $6 \times 10^{-4}$, a value consistent with a complexity of 1250 nucleotides contributed by the α- plus β-globin sequences in our cDNA probe. Axel, R., et al., Cell 7: 247–254 (1976).

This rabbit globin cDNA was used as a probe in hybridization reactions with total RNA isolated from six transformed cell lines. Total RNA from transformed clone 6 protected 44% of the rabbit cDNA at completion, the value expected if only β-gene transcripts were present. This reaction displayed pseudo-first-order kinetics with $R_0t_{1/2}$ of $2 \times 10^3$. A second transformant reacted with an $R_0t_{1/2}$ of $8 \times 10^3$. No significant hybridization was observed at $R_0ts \geq 10^4$ with total RNA preparations from the four additional transformants.

We have characterized the RNA from clone 6 in greatest detail. RNA from this transformant was fractionated into nuclear and cytoplasmic populations to determine the intracellular localization of the rabbit globin RNA. The cytoplasmic RNA was further fractionated by oligo (dT)-cellulose chromatography into poly (A)+ and poly (A)− RNA. Poly (A)+ cytoplasmic RNA from clone 6 hybridizes with the rabbit cDNA with an $R_0t_{1/2}$ of 25. This value is 1/80th of the $R_0t_{1/2}$ observed with total cellular RNA, consistent with the observation that poly (A)+ cytoplasmic RNA is 1–2% of the total RNA in a mouse cel. Hybridization is not detectable with either nuclear RNA or cytoplasmic poly (A)− RNA at $R_0t$ values of $1 \times 10^4$ and $2 \times 10^4$, respectively. The steady-state concentration of rabbit β-globin RNA present in our transformant can be calculated from the $R_0t_{1/2}$ to be about five copies per cell, with greater than 90% localized in the cytoplasm.

Several independent experiments argue that the globin RNA detected derives from transcription of the rabbit DNA sequences present in this transformant: (i) cDNA was prepared from purified 9S mouse globin RNA. This cDNA does not hybridize with poly (A)+ RNA from clone 6 at $R_0t$ values at which the reaction with rabbit globin cDNA is complete (ii) Rabbit globin cDNA does not hybridize with total cellular RNA obtained with tk+ globin− transformants at $R_0t$ values exceding $10^4$. (iii) The hybridization observed does not result from duplex formation with rabbit globin DNA possibly contaminating the RNA preparations. Rabbit cDNA was annealed with total cellular RNA from clone 6, the reaction product was treated with S1 nuclease, and the duplex was subjected to equilibrium density centrifugation in cesium sulfate under conditions that separate DNA-RNA hybrids from duplex DNA. The S1-resistant cDNA banded at a density of 1.54 g/ml, as expected for DNA-RNA hybrid structures. These data, along with the observation that globin RNA is polyadenylated, demonstrate that the hybridization observed with RNA preparations does not result from contaminating DNA sequences.

CHARACTERIZATION OF RABBIT GLOBIN TRANSCRIPTS IN TRANSFORMED CELLS

In rabbit erythroblast nuclei, the β-globin gene sequences are detected as a 14S precursor RNA that reflects transcription of two intervening sequences that are subsequently removed from this molecule to generate a 9S messenger RNA. It was therefore of interest to determine whether the globin transcripts detected exist at a discrete 9S species, which is likely to reflect appropriate splicing of the rabbit gene transcript by the mouse fibroblast. Cytoplasmic poly (A)-containing RNA from clone 6 was electrophoresed on a methyl-mercury/agarose gel, Bailey, J. & Davidson, N., Anal. Biochem. 70: 75–85 (1976), and transferred to diazotized cellulose paper. Alwine, J. C. et al., Proc. Natl. Acad. Sci. USA 74: 5340–5454 (1977). After transfer, the RNA on the filters was hybridized with DNA from the plasmid pβG1, which contains rabbit β-globin cDNA sequences. Maniatis, T., et al., Cell 8: 163–182 (1976). Using this $^{32}$P-labeled probe, a discrete 9S species of RNA was observed in the cytoplasm of the transformant, which comigrated with rabbit globin mRNA isolated from rabbit erythroblasts. Hybridization to 9S RNA species was not observed in parallel lanes containing either purified mouse 9S globin RNA or poly (A)-containing cytoplasmic RNA from a tk+ transformant containing no rabbit globin genes.

In these experiments, it was not possible to detect the presence of a 14S precursor in nuclear RNA populations from the transformants. This is not surprising, because the levels expected in nuclear RNA, given the observed cytoplasmic concentration, are likely to be below the limits of detection of this techniques. The 5' and 3' boundaries of the rabbit globin sequences expressed in tranformed fibroblasts along with the internal processing sites can be defined more accurately by hybridizing this RNA with cloned DNAs, followed by S1 nuclease digestion and subsequent gel analysis of the DNA products. Berk, A. J. & Sharp, P. A., Cell 12: 721–732 (1977). When β-globin mRNA from rabbit erythroid cells was hybridized with cDNA clone pβG1 under appropriate conditions, the entire 576-base pair insert of cDNA was protected from S1 nuclease attack. When the cDNA clone was hybridized with RNA from our transformant, surprisingly, a discrete DNA band was observed at 525 base pairs, but not at 576 base pairs. These results suggest that, in this transformant, rabbit globin RNA molecules are present that have a deletion in a portion of the globin mRNA sequence at the 5' or 3' termini. To distinguish between these possibilities, DNA of the λ clone, RβG1, containing the chromosomal rabbit β-globin sequence hybridized with transformed fibroblast RNA. The hybrid formed was treated with S1 nuclease, and the protected DNA fragments were analyzed by alkaline agarose gel electrophoresis and identified by Southern blotting procedures. Southern, E. M., J. Mol. Biol. 98: 503–517 (1975). Because the rabbit β-globin gene is interrupted by two intervening sequences, the hybridization of mature rabbit mRNA to RβG1 DNA generates three DNA fragments in this sort of analysis: a 146-base pair fragment spanning the 5' terminus to the junction of the small intervening sequence, a 222-base pair internal fragment bridging the small and large intervening sequences, and a 221-base pair fragment spanning the 3' junction of the large intervening sequence of the 3' terminus of the mRNA molecule. When transformant RNA was analyzed in this fashion, a 222-base pair fragment was observed as well as an aberrant fragment of 100 base pairs but no 146-base pair fragment. Hybridization with a specific 5' probe showed that the internal 222 base pair fragment was present. The sum of the protected lengths equaled the length of the DNA fragment protected by using the cDNA clone. Taken together, these results indicate that although the intervening sequences expressed in transformed mouse fibroblast are removed from the RNA transcripts precisely, the 5' termini of the cytoplasmic transcripts observed do not contain about 48±5 nucleotides present in mature 9S RNA of rabbit erythroblasts.

DISCUSSION

In these studies, mouse cell lines have been constructed that contain the rabbit β-globin gene. The ability of the mouse fibroblast recipient to transcribe and process this heterologous gene has then been analyzed. Solution hydbridization experiments in concert with RNA blotting techniques indicate that, in at least one transformed cell line, rabbit globin sequences are expressed in the cytoplasm as a polyadenylylated 9S species. Correct processing of the rabbit β-globin gene has also been observed in tk+ mouse cell transformants in which the globin and tk plasmids have been ligated prior to transformation. Mantei, N., et al., Nature (London) 281: 40–46 (1970). Similar results have been obtained by using a viral vector to introduce the rabbit globin gene into monkey cells. Hamer, D. H. & Leder, P., Nature (London), 281: 35–39 (1979); Mulligan, R. C., et al., Nature (London) 277: 108–114 (1979). Taken together, these results suggest that nonerythroid cells from heterologous species contain the enzymes necessary to correctly process the intervening sequences of a rabbit gene whose expression usually is restricted to erythroid cells.

The level of expression of rabbit globin sequences in the transformant is low: five copies of globin RNA are present in the cytoplasm of each cell. The results indicate that the two intervening sequences present in the original globin transcript are processed and removed at loci indistinguishable from those observed in rabbit erythroid cells. Surprisingly, 45 nucleotides present at the 5' terminus of mature rabbit mRNA are absent from the β-globin RNA sequence detected in the cytoplasm of the transformant examined. It is possible that incorrect initiation of transcription occurs about the globin gene in this mouse cell lines. Alternatively, the globin sequences detected may result from transcription of a long precursor that ultimately must undergo 5' processing to generate the mature 9S species. Incorrect processing at the 5' terminus in the mouse fibroblast could be responsible for the results. At present, it is difficult to distinguish among these alternatives. Because the analysis is restricted to a single transformant, it is not known whether these observations are common to all transformants expressing the globin gene or reflect a rare, but interesting abberation. It should be noted, however, that in similar experiments by Weissman and his colleagues, Mantei, N., et al., Nature (London) 281: 40–46 (1979), at least a portion of the rabbit globin RNA molecules transcribed in transformed mouse fibroblasts retain the correct 5' terminus.

Several alternative explanations can be offered for the expression of globin sequences in transformed fibroblasts. It is possible that constitutive synthesis of globin RNA occurs in cultured fibroblasts, Humphries, S., et al., Cell 7: 267-277 (1976), at levels five to six orders of magnitude below the level observed in erythroblasts. The introduction of 20 additional globin DNA templates may simply increase this constitutive transcription to the levels observed in the transformant. Alternatively, it is possible that the homologous globin gene is repressed by factors that are partially overcome by a gene dosage effect provided by the introduction of 20 additional globin genes. Finally, normal repression of the globin gene in a fibroblast may depend upon the position of these sequences in the chromosome. At least some of the newly introduced genes are likely to reside at loci distant from the resident mouse globin genes. Some of these ectopic sites may support low level transcription. Present data do not permit one to distinguish among these and other alternatives.

Although the number of rabbit globin genes within a given transformant remains stable for over a hundred generations of culture in hypoxanthine/aminopterin/-thymidine, it has not been possible to prove that these sequences are covalently integrated into recipient cell DNA. In previous studies, however, it has been demonstrated that cotransformation of either ΦX174 or plasmid pBR322 results in the stable integration of these sequences into high molecular nuclear DNA. In the present study, the globin gene represents a small internal segment of the high molecular weight concatenated phage DNA used in the transformation. Analysis of integration sites covalently linked to donor DNA is therefore difficult. Preliminary studies using radioactive λ sequences as a probe in DNA blotting experiments indicate that, in some cell lines, a contiguous stretch of recombinant phage DNA with a minimum length of 50 kbp has been introduced.

The presence of 9S globin RNA in the cytoplasm of transformants suggests that this RNA may be translated to give rabbit β-globin polypeptide. Attempts to detect this protein in cell lysates using a purified anti-rabbit β-globin antibody have thus far been unsuccessful. It is possible that the globin RNAs in the transformant are not translated or are translated with very low efficiency due to the absence of a functional ribosomal binding site. The cytoplasmic globin transcripts in the transformant lack about 48 nucleotides of untranslated 5' sequence, which includes 13 nucleotides known to interact with the 40S ribosomal subunit in nuclease protection studies. Efstratiadis, A., et al., Cell 10: 571-585 (1977); Legon, S., J. Mol. Biol. 106: 37-53 (1976). Even if translation did occur with normal efficiency, it is probable that the protein would exist at levels below the limits of detection of the immunologic assay due to the low level of globin RNA, and the observation that the half-life of β-globin in the absence of heme and globin may be less than 30 min. Mulligan, R. C., et al., Nature (London) 277: 108-114 (1979).

These studies indicate the potential value of cotransformation systems in the analysis of eucaryotic gene expression. The introduction of wild-type genes along with native and in vitro-constructed mutant genes into cultured cells provides an assay for the functional significance of sequence organization. It is obvious from these studies that this analysis will be facilitated by the ability to extend the generality of cotransformation to recipient cell lines, such as murine erythroleukemia cells, that provide a more appropriate environment for the study of heterologous globin gene expression.

THIRD SERIES OF EXPERIMENTS

The cotransformation experiments involving transformation of mouse cells with rabbit β-globin and with plasmid pBR322 and ΦX-174 DNA were continued and extended with the following results.

ΦX DNA was used in cotransformation experiments with the tk gene as the selectable marker. ΦX replicative from DNA was cleaved with Pst I, which recognizes a single site in the circular genome, Sanger, F. et al., Nature 265: 687-695 (1977). Purified tk gene (500 pg) was mixed with 1-10 μg of Pst-cleaved ΦX replicative form DNA. This DNA was then added to mouse Ltk⁻ cells using the transformation conditions described herein and in Wigler, M., et al., Cell 16:777-785 (1979). After two weeks in selective medium (HAT), tk+ transformants were observed at a frequency of one colony per $10^6$ cells per 20 pg of purified gene. Clones were picked and grown into mass culture.

It was then asked whether $tk^{30}$ transformants contained ΦX DNA sequences. High molecular weight DNA from the transformants was cleaved with the restriction endonuclease Eco RI, which recognizes no sites in the ΦX genome. The DNA was fractionated by agarose gel electrophoresis and transferred to nitrocellulose filters, and these filters were then annealed with nick-translated $^{32}$P-ΦX DNA (blot hybridization).

These annealing experiments indicated that 15 to 16 transformants acquired bacteriophage sequences. Since the ΦX genome is not cut with the enzyme Eco RI, the number of bands observed reflects the minimum number of eucaryotic DNA fragments containing information homologous to ΦX. The clones contain variable amounts of ΦX sequences: 4 of the 15 positive clones reveal only a single annealing fragment while others reveal at least fifty ΦX-specific fragments.

It should be noted that none of 15 clones picked at random from neutral medium, following exposure to tk and ΦX DNA, contain ΦX information. Transformation with ΦX therefore is restricted to a subpopulation of tk+ transformants. The addition of a selectable marker therefore facilitates the identification of cotransformants.

TRANSFORMATION OF MOUSE CELLS WITH THE RABBIT β-GLOBIN GENE

Transformation with purified eucaryotic genes provides a means for studying the expression of cloned genes in a heterologous host. Cotransformation experiments were performed with the rabbit β major globin gene which was isolated from a cloned library of rabbit chromosomal DNA. One β-globin clone, designated R G-1 consists of a 15 kb rabbit DNA fragment carried on the bacteriophage λ cloning vector Charon 4A. Intact DNA from this clone (RβG-1) was mixed with the viral tk DNA at a molar ratio of 100:1, and tk+ transformants were isolated and examined for the presence of rabbit globin sequences. Cleavage of RβG-1 with the enzyme Kpn I generates a 4.7 kb fragment which contains the entire rabbit β-globin gene. This fragment was purified by gel electrophoresis and nick-translated to generate a probe for subsequent annealing experiments. The β-globin genes of mouse and rabbit are partially homologous, although we do not observe annealing of the rabbit β-globin probe with Kpn-cleaved mouse DNA, presumably because Kpn generates very large globin-specific fragments. In contrast, cleavage of rabbit liver DNA with Kpn I generates the expected 4.7 kb globin band. Cleavage of transformed cell DNA with the enzyme Kpn I generates a 4.7 kb fragment containing globin-specific information in six of the eight tk+ transformants examined. The number of rabbit globin genes present in these transformants is variable. In comparison with controls, some of the clones contain a single copy of the gene, while others may contain as many as 20 copies of this heterologous gene.

RABBIT β-GLOBIN SEQUENCES ARE TRANSCRIBED IN MOUSE TRANSFORMANTS

The cotransformation system developed provides a functional assay for cloned eucaryotic genes if these genes are expressed in the heterologous recipient cell. Six transformed cell clones were analyzed for the presence of rabbit β-globin RNA sequences. In initial experiments, solution hybridization reactions were performed to determine the cellular concentration of rabbit globin transcripts in transformants.

A radioactive cDNA copy of purified rabbit α and β-globin mRNA was annealed with a vast excess of total cellular RNA from transformants under experimental conditions such that rabbit globin cDNA does not form a stable hybrid with mouse sequences. Total RNA from transformed clone 6 protects 44% of the rabbit cDNA at completion, the value expected if only β gene transcripts are present. This reaction displays pseudo-first-order kinetics with an $R_oT_{1/2}$ of $2\times 10^3$. A second transformant (clone 2) reacts with an $R_ot_{1/2}$ of $8\times 10^3$. No significant hybridization was observed with total RNA preparations from four other transformants. Further analysis of clone 6 demonstrates that virtually all of the rabbit β-globin RNA detected in this transformant is polyadenylated and exists at a steady state concentration of about five copies per cell with greater than 90% of the sequences localized in the cytoplasm.

GLOBIN SEQUENCES EXIST AS A DISCRETE 9S SPECIES IN TRANSFORMED CELLS

In rabbit erythroblast nuclei, the β-globin gene sequences are detected as a 14S precursor RNA which reflects transcription of two intervening sequences which are subsequently spliced from this molecule to generate a 9S messenger RNA. Our solution hybridization experiments only indicate that polyadenylated rabbit globin RNA sequences are present in the mouse transformant. It was therefore of interest to determine whether the globin transcripts we detected exist as a discrete 9S species, which is likely to reflect appropriate splicing of the rabbit gene transcript by the mouse fibroblast. Cytoplasmic poly A-containing RNA from clone 6 was denatured by treatment with 6M urea at 70° C., and electrophoresed on a 1% acid-urea-agarose gel and transferred to diazotized cellulose paper. Following transfer, the RNA filters were hybridized with DNA from the plasmid RβG-1 containing rabbit β-globin cDNA sequences. Using this =P-labeled probe, a discrete 9S species of cytoplasmic RNA is seen which co-migrates with rabbit globin mRNA isolated from rabbit erythroblasts. Hybridization to 9S RNA species is not observed in parallel lanes containing either purified mouse 9S globin RNA or polyadenylated cytoplasmic RNA from a tk+ transformant containing no rabbit globin genes.

One is unable in these experiments to detect the presence of a 14S precursor in nuclear RNA populations from the transformant. This is not surprising, since the levels expected in nuclear RNA, given the observed cytoplasmic concentration, are likely to be below the limits of detection of this technique. Nevertheless, the results with cytoplasmic RNA strongly suggest that the mouse fibroblast is capable of processing a transcript of the rabbit β-globin gene to generate a 9S polyadenylated species which is indistinguishable from the β-globin mRNA in rabbit erythroblasts.

RESCUE OF pBR 322 DNA FROM TRANSFORMED MOUSE CELLS

Observations on cotransformation were extended to the Ek-2 approved bacterial vector, plasmid pBR 322. Using the cotransformation scheme outlined herein, cell lines were constructed containing multiple copies of the pBR 322 genome. Blot hybridization analyses indicate that the pBR 322 sequences integrate into cellular DNA without significant loss of plasmid DNA. pBR 322 DNA linearized with either Hind III or Bam HI, which destroys the tetracycline resistance gene, integrates into mouse DNA with retention of both the plasmid replication origin and the ampicillin resistance (β-lactamase) gene. It was therefore asked whether these plasmid sequences could be rescued from the mouse genome by a second transformation of bacterial cells.

The experimental approach chosen is outlined in FIG. 2. Linearized pBR 322 DNA is introduced into mouse Ltk− cells via cotransformation using the tk gene as a selectable marker. DNA is isolated from transformants and screened for the presence of pBR 322 sequences. Since the donor plasmid is linearized, interrupting the tetracycline resistant gene, transformed cell DNA contains a linear stretch of plasmid DNA consisting of the replication origin and the β-lactamase gene covalently linked to mouse cellular DNA. This DNA is cleaved with an enzyme such as Xho I, which does not digest the plasmid genome. The resulting fragments are circularized at low DNA concentrations in the presence of ligase. Circular molecules containing plasmid DNA are selected from the vast excess of eucaryotic circles by transformation of E. coli strain χ1776.

This series of experiments has been carried out and a recombinant plasmid isolated from transformed mouse cell DNA which displays the following properties: (1) The rescued plasmid is ampicillin resistant, but tetracycline sensitive consistent with the fact that the donor pBR 322 was linearized by cleavage within the tetracycline resistance gene. (2) The rescue plasmid is 1.9 kb larger than pBR 322 and therefore contains additional DNA. (3) The rescued plasmid anneals to a single band in blot hybridizations to Eco RI-cleaved mouse liver DNA, suggesting that the plasmid contains an insert of single copy mouse DNA. These observations demonstrate that bacterial plasmids stably integrated into the mouse genome via transformation, can be rescued from this unnatural environment, and retain their ability to function in bacterial hosts.

This result immediately suggests modified schemes utilizing plasmid rescue to isolate virtually any cellular gene for which selective growth criteria are available. The aprt gene of the chicken is not cleaved by Hind III or Xho I and transformation of aprt− mouse cells with cellular DNA digested with these enzymes results in the generation of aprt+ colonies which express the chicken aprt gene. Ligation of Hind III cleaved chicken DNA with Hind III cleaved pBR 322 results in the formation of hybrid DNA molecules, in which the aprt gene is now adjacent to plasmid sequences. Transformation of aprt− cells is now performed with this DNA. Transformants should contain the aprt gene covalently linked to pBR 322, integrated into the mouse genome. This transformed cell DNA is now treated with an enzyme which does not cleave either pBR 322 or the aprt gene, and the resultant fragments are circularized with ligase. Transformation of E. coli with these circular molecules should select for plasmid sequences from eucaryotic DNA and enormously enrich for chicken aprt sequences. This double selection technique permits the isolation of genes expressed at low levels in eucaryotic cells, for which hybridization probes are not readily obtained.

DISCUSSION

The frequency with which DNA is stably introduced into competent cells is high. Furthermore, the cotransformed sequences appear to be integrated into high molecular weight nuclear DNA. The number of integration events varies from one to greater than fifty in independent transformed clones. At present, precise statements cannot be made concerning the nature of the integration intermediate. Although data with ΦX are in accord with the model in which ΦX DNA integrates as a linear molecule, it is possible that more complex intramolecular recombination events generating circular intermediates may have occurred prior to or during the integration process. Whatever the mode of integration, it appears that cells can be stably transformed with long stretches of donor DNA. It has been observed that transformants contain continguous stretches of donor DNA 50 kb long. Furthermore, the frequency of competent cells in culture is also high. At least one percent of the mouse Ltk− cell recipients can be transformed to the tk+ phenotype. Although the frequency of transformation in nature is not known, this process could have profound physiologic and evolutionary consequences.

The introduction of cloned eucaryotic genes into animal cells provides an in vivo system to study the functional significance of various features of DNA sequence organization. In these studies, stable mouse cell lines have been constructed which contain up to 20 copies of the rabbit β-globin gene. The ability of the mouse fibroblast recipient to transcribe and process this heterologous gene has been analyzed. Solution hybridization experiments in concert with RNA blotting techniques indicate that in at least one transformed cell line, rabbit globin sequences are expressed in the cytoplasm as a 9S species indistinguishable from the mature messenger RNA of rabbit erythroblasts. These results suggest that the mouse fibroblast contains the enzymes necessary to transcribe and correctly process a rabbit gene whose expression is normally restricted to erythroid cells. Similar observations have been made by others using a viral vector to introduce the rabbit globin gene into monkey cells.

These studies indicate the potential value of cotransformation systems in the analysis of eucaryotic gene expression. The introduction of wild type genes along with native and in vitro constructed mutant genes into cultured cells provides an assay for the functional significance of sequence organization. It is obvious from these studies that this analysis will be facilitated by the ability to extend the generality of cotransformation to recipient cell lines, such as murine erythroleukemia cells, which may provide a more appropriate environment for the study of heterologous globin gene expression.

FOURTH SERIES OF EXPERIMENTS

The ability to transfer purified genes into cultured cells provides the unique opportunity to study the function and physical state of exogenous genes in the transformed host. The development of a system for DNA-mediated transfer of the HSV thymidine kinase (tk) gene to mutant mouse cells, Wigler, M., et al., Cell 11:223-232 (1977), has permitted extension of these studies to unique cellular genes. Wigler, M., et al., Cell 14:725-731 (1979). It has been found that high molecular weight DNA obtained from tk+ tissues and cultured cells from a variety of eucaryotic organisms can be used to transfer tk activity to mutant mouse cells deficient in this enzyme. The generality of the transformation process has been demonetrated by the successful transfer of the cellular adenine phosphoribosyl transferase (aprt) gene and the hypoxanthine phosphoribosyl transferase (hprt) gene. Wigler, M., et al., Proc. Nat. Acad. Sci. USA 76:1373-1376 (1979); Willicke, K., et al., Molec. Gen. Genet. 170:179-185 (1979); Graf, L. Y., et al., Somatic Cell Genetics, in press (1979).

More recently, it has been demonstrated that cells transformed with genes coding for selectable biochemical markers also integrate other physically unlinked DNA fragments at high frequency. In this manner, the tk gene has been used as a marker to identify mammalian cells cotransformed with defined procaryotic and eucaryotic genes into cultured mammalian cells. Wigler, M., et al., Cell 16:777-785 (1979).

Detection of gene transfer has in the past relied extensively on the use of appropriate mutant cell lines. In some cases, cells resistant to metabolic inhibitors contain dominant acting mutant genes. Cotransformation with such dominant acting markers should in principle permit the introduction of virtually any cloned genetic element into wild type cultured cells. In this study, cells were transformed with the gene coding for a mutant dihydrofolate reductase (dhfr) gene which renders cells resistant to high concentrations of methotrexate (mtx). Flintoff, W. F., et al., Cell 2:245-262 (1976).

Cultured mammalian cells are exquisitely sensitive to the folate antagonist, methotrexate. Mtx resistant cell lines have been identified which fall into three categories: (1) cells with decreased transport of this drug. Fischer, G. A. Biochem. Pharmacol. 11:1233-1237 (1962); Sirotnak, F. M., et al., Cancer Res. 28:75-80 (1968); (2) cells with structural mutations which lower the affinity of dhfr for methotrexate. Flintoff, W. F., et al., Cell 2:245-262 (1976); and (3) cells which produce inordinately high levels of dhfr. Biedler, J. L., et al., Cancer Res. 32: 152-161 (1972); Chang, S. E., and Littlefield, J. W., Cell 7:391-396 (1976). Where they have been examined, cells producing high levels of dhfr have been found to contain elevated levels of the dhfr gene (gene amplification). Schimke, R. T., et al, Science 202:1051-1055 (1978).

An interesting methotrexate resistant variant cell line (A29) has been identified that synthesizes elevated levels of a mutant dihydrofolate reductase with reduced affinity for methotrexate. Wigler, M., et al., Cell 16:777-785 (1979). Genomic DNA from this cell line has been used as donor in experiments to transfer the mutant dhfr gene to mtx sensitive cells. Exposure of mtx resistant transformed cells to increasing levels of mtx selects for cells which have amplified the transferred gene. In this way, it is possible to transfer and amplify

TRANSFER OF THE MUTANT HAMSTER DIHYDROFOLATE REDUCTASE GENE TO MOUSE CELLS

High molecular weight cellular DNA was prepared from wildtype mtx sensitive CHO cells and from A29 cells, an mtx resistant CHO derivative synthesizing increased levels of a mutant dhfr. Flintoff, W. F., et al., Cell 2:245–262 (1976). The ability of these DNA preparations to transfer either the dhfr gene or the tk gene to tk$^-$ mouse L cells (Ltk$^-$ aprt$^-$) was tested using a modification of the calcium phosphate coprecipitation method. Wigler, M., et al., Proc. Nat. Acad. Sci. USA 76:1373–1376 (1979). DNA from both mutant A29 and wild-type CHO cells was competent in transferring the tk gene to Ltk$^-$ aprt$^-$ cells. Methotrexate resistant colonies were observed only following treatment of cells with DNA from A29. The data obtained suggest that treatment of methotrexate sensitive cells with A29 DNA resulted in the transfer and expression of a mutant dhfr gene, thus rendering these cells insensitive to elevated levels of methotrexate.

In order to test this hypothesis directly, molecular hybridization studies were performed to demonstrate the presence of the hamster dhfr gene in DNA from presumed transformants. A mouse dhfr cDNA clone (pdfr-21), Chang, A.C.Y., et al., Nature 275:617–624 (1978), that shares homology with the structural gene sequences of the hamster dhfr gene was used to detect the presence of this gene in our transformants. Restriction analysis of the dhfr gene from A29, from presumed transformants, and from amplified mouse cells, was performed by blot hybridization. Southern, E. M., J. Mol. Biol. 98:503–517 (1975). DNA was cleaved with restriction endonuclease Hind III, electrophoresed in agarose gels, and transferred to nitrocellulose filters. These fileres were then hybridized with high specific activity, $^{32}$P-labeled nick-translated pdhfr-21 and developed by autoradiography. This procedure visualizes restriction fragments of genomic DNA homologous to the dhfr probe. Prominent bands are observed at 15 kb, 3.5 kb and 3 kb for mouse DNA and 17 kb, 7.9 kb, 3.7 kb and 1.4 kb for hamster DNA. The restriction profiles between these two species and sufficiently different to permit one to distinguish the hamster gene in the presence of an endogenous mouse gene. Five L cell transformants resistant to methotrexate were therefore examined by blot hybridization. In each transformed cell line, one observed the expected profile of bands resulting from cleavage of the endogenous mouse dhfr gene and a series of additional bands whose molecular weights are identical to those observed upon cleavage of hamster DNA. The 17.9 kb, 7.9 kb and 1.4 kb bands observed in hamster DNA are diagostic for the presence of the hamster dhfr gene and are present in all transformants.

In initial experiments, the lowest concentration of methotrexate (0.1 μg per ml) was chosen which would decrease survival of Ltk$^-$ aprt$^-$ cells to less than $10^{-7}$. Previous studies, Flintoff, W. F., et al., Cell 2:245–262 (1976), suggested that the presence of a single mutant dhfr gene can render cells resistant to this concentration of methotrexate. Comparison of the intensity of the hamster dhfr gene fragments of transformed cell DNA with those of wild-type hamster DNA suggest that our transformants contain one or at most a few methotrexate resistant hamster genes. By contrast, donor A29 cells, which have been shown to produce elevated levels of the mutant dhfr, Flintoff, W. F., et al., Cell 2:245–262 (1976), appear to contain multiple copies of this gene.

AMPLIFICATION OF THE TRANSFERRED dhfr GENE

Initial transformants were selected for resistance to relatively low levels of mtx (0.1 μg/ml). For every clone, however, it was possible to select cells resistant to elevated levels of mtx by exposing mass cultures to successively increasing concentrations of this drug. In this manner, we isolated cultures resistant to up to 40 μg/ml of methotrexate starting from clones that were initially resistant to 0.1 μg/ml. We next asked if increased resistance to methtrexate in these transformants was associated with amplification of a dhfr gene and, if so, whether the endogenous mouse or the newly transferred hamster gene was amplified. DNA from four independent isolates and their resistant derivatives was examined by blot hybridization. In each instance, enhanced resistance to methotrexate was accompanied by an increase in the copy number of the hamster gene. This is most readily seen by comparing the intensities of the 1.5 kb band. In no instance have we detected amplification of the endogenous mouse dhfr gene. Lastly, it is noted that not all lines selected at equivalent methotrexate concentrations appear to have the same dhfr gene copy number.

THE dhfr GENE AS A GENERALIZED TRANSFORMATION VECTOR

Selectable genes can be used as vectors for the introduction of other genetic elements into cultured cells. In previous studies, it has been demonstrated that cells transformed with the tk gene are likely to incorporate other unlinked genes. Wigler, M., et al., Cell 16:777–785 (1979). The generality of this approach was tested for the selectable marker, the mutant dhfr gene. 20 μg of total cellular DNA from A29 was mixed with 1 μg of Hind III-linearized pBR 322 DNA. Recipient cells were exposed to this DNA mixture and, after two weeks, methotrexate resistant colonies were picked. Genomic DNA from transformants was isolated, cleaved with Hind III and analyzed for the presence of pBR322 sequences. Two independent isolates were examined in this way and in both cases multiple copies of pBR322 sequences were present in these methotrexate transformants.

An alternate approach to generalized transformation involves ligation of a nonselectable DNA sequence to a selectable gene. Since the muant dhfr gene is a dominant acting drug resistance factor, this gene is an ideal vector. Furthermore, it should be possible to amplify any genetic element ligated to this vector by selecting cells resistant to elevated levels of mtx. To explore this possibility, restriction endonucleases that do not destroy the dhfr gene of A29 were identified by transformation assay. One such restriction endonuclease, Sal I, does not destroy the transformation potential of A29 DNA. Sal I-cleaved A29 DNA was therefore ligated to an equal mass of Sal I-linearized pBR32. This ligation product was subsequently used in transformation experiments. Methotrexate resistant colonies were picked and grown into mass culture at 0.1 μg methotrexate/ml. Mass cultures were subsequently exposed to increasing concentrations of methotrexate.

DNAs were obtained from mass cultures resistant to 0.1, 2, 10 and 40 μg/ml methotrexate, and the copy number of pBR322 and dhfr sequences was determined by blot hybridization. Six independent transformed lines were examined in this fashion. Five of these lines exhibited multiple bands homologous to pBR322 sequences. In four of these transformed clones, at least one of the pBR 322-specific bands increased in intensity upon amplification of dhfr. In SS-1, two pBR322-specific bands are observed in DNA from cells resistant to 0.1 μg/ml methotrexate. These bands increase several-fold in intensity in cells resistant to 2 μg/ml. No further increase in intensity is observed, however, in cells selected for resistance to 40 μg/ml/ In a second line, SS-6, all pBR 322 bands present at 0.1 μg/ml continue to increase in intensity as cells are selected first at 2 μg/ml and then at 40 μg/ml methotrexate. Curiously, new pBR322-specific bands appear after selection at higher methotrexate concentrations. It was estimated that there is at least a fifty-fold increase in copy number for pBR322 sequences in this cell line. In a third cell line, HH-1, two pBR322-specific bands increase in intensity upon amplification, others remain constant or decrease in intensity. Thus, the pattern of amplification of pBR322 sequences observed in these cells can be quite varied. Nevertheless, it appears that the mutant dhfr gene can be used as vector for the introduction and amplification of defined DNA sequences into cultured animal cells.

DISCUSSION

The potential usefulness of DNA-mediated transformation in the study of eucaryotic gene expression depends to a large extend on its generality. Cellular genes coding for selectable biochemical functions have previously been introduced into mutant cultured cells, Wigler, M., et al., Cell 14:725-731 (1979); Wigler, M., et al., Proc. Nat. Acad. Sci. USA 76:1373-1376 (1979); Wilecke, K., et al., Molec, Gen. Genet. 170:179-185 (1979); Graf, L. H., et al., Somatic Cell Genetics, in press (1979). In the present study, a dominant acting, methotrexate resistant dhfr gene has been transferred to wild-type cultured cells. The use of this gene as a vector in cotransformation systems may now permit the introduction of virtually any genetic element into a host of new cellular environments.

In initial experiments, DNA from A29 cells, a methotrexate resistant CHO derivative synthesizing a mutant dhfr was added to cultures of mouse L cells. Methotrexate resistant colonies appeared at a frequency of one to ten colonies/$5 \times 10^5$ cells/20 μg cellular DNA. No colonies were observed upon transformation with DNA obtained from wild-type, methotrexate sensitive cells, although this DNA was a competent donor of the thymidine kinase gene. Definitive evidence that we have effected transfer of a mutant hamster dhfr gene was obtained by demonstrating the presence of the hamster gene in mouse transformants. The restriction maps of the mouse and hamster dhfr genes are significantly different and permit one to distinguish these genes in blot hybridization experiments. In all transformants examined, one observes two sets of restriction fragments homologous to a mouse dhfr cDNA clone: a series of bands characteristic of the endogenous mouse gene and a second series characteristic of the donor hamster gene.

The utility of transformation of the dhfr locus is a function of the relative frequencies both of transformation and of spontaneous resistance to mtx. The demonstration that all mtx resistant L cells picked result from transformation rather than amplification of endogenous genes suggests that amplification of dhfr is a rare event in this cell line. Attempts were made to transform other cell lines, including mouse teratoma and rat liver cells and, in these instances, hybridization studies reveal that the acquisition of mtx resistance results from amplification of endogenous dhfr genes. The use of a purified dhfr gene is likely to overcome these difficulties by enormously increasing the frequency of transformation.

The dhfr copy number observed in initial transformants is low. This observation is consistent with previous studies suggesting that a single mutant dhfr gene is capable of rendering cells mtx resistant under selective criteria (0.1 μ/ml mtx). Flintoff, W. F., et al., Cell 2: 245-262 (1976). Exposure of these initial mtx resistant transformants to stepwise increases in drug concentration results in the selection of cells with enhanced mtx resistance resulting from amplification of the newly transferred mutant hamster dhfr gene. In no transformants has amplification of the endogenous mouse gene been observed in response to selective pressure. It is likely that a single mutant gene affords significantly greater resistance to a given concentration of mtx than a single wild-type gene. If the frequency of the amplification is low, one is merely selecting resistance variants having the minimum number of amplification events. It is also possible that newly transferred genes may be amplified more readily than endogenous genes.

The mutant dhfr gene has been used as a dominant transfer vector to introduce nonselectable genetic elements into cultured cells. One experimental approach exploits the observation made previously, Wigler, M., et al.; Cell 16: 777-785 (1979), that competent cells integrate other physically unlinked genes at high frequency. Cultures exposed to pBR322 DNA, along with the genomic DNA containing the mutant dhfr gene give rise to mtx resistant cell lines containing multiple copies of the bacterial plasmid.

An alternative approach to genetic vectoring involves ligation of pBR322 sequences to the selectable dhfr gene prior to transformations. This procedure also generates transformants containing multiple pBR322 sequences. Amplification of dhfr genes results in amplification of pBR322 sequences, but the patterns of amplification differ among cell lines. In one instance, all pBR322 sequences amplify with increasing mtx concentrations. In other lines, only a subset of the sequences amplify.

In yet other lines, sequences appear to have been lost or rearranged. In some lines, amplification proceeds with increasing mtx concentrations up to 40 μ/ml, whereas in others, amplification ceases at 2 μg/ml. At present, the amplification process is not understood nor has the amplification unit been defined. Whatever the mechanisms responsible for these complex events, it is apparent that they can be expolited to control the dosage of virtually any gene introduced into cultured cells.

FIFTH SERIES OF EXPERIMENTS

Mouse teratocarcinoma (TCC) stem cells provide a unique vector for the introduction of specific, predetermined, genetic changes into mice. Mintz, B. & Illmensee, K., Proc. Natl. Acad. Sci. 72: 3585-3589 (1975); Mintz, B., Brookhaven Symp. Biol. 29: 82-85 (1977). These cells lose their neoplastic properties and undergo normal differentiation when placed in the environment of the early embryo. There they can contribute to formation of all somatic tissues in a mosaic animal comprising both donor- and host-derived cells, and also to the germ line, from which the progeny have genes of the tumor strain in all their cells. Thus, during initial propagation of TCC stem cells in culture, clones with experimentally selected nuclear, Dewey, M. J., et al., Proc. Natl. Acad. Sci., 74: 5564–5568 (1977), and cytoplasmic, Watanabe, T., et al., Proc. Natl. Acad. Sci., 75: 5113–5117 (1978), gene mutations have been obtained and the cells have proved capable of participating in embryogenesis.

The effective application of this system in probing the control of gene expression during differentiation would be greatly enhanced if, as proposed, Mintz, B., Differentiation 13: 25–27 (1979), precisely defined genes, either in native or modified form, with known associated sequences, could be introduced into developmentally totipotent TCC cells prior to their development in vivo. DNA-mediated gene transfer into cultured mouse cells has now been reported for a variety of viral and cellular genes coding for selectable biochemical functions. The purified viral thymidine kinase (tk; ATP: thymidine 5'-phosphotransferase, EC 2.7.1.21) gene has provided a model system for gene transfer, Wigler, M. et al., Cell 11: 223–232 (1977), and has been followed by the DNA-mediated transfer of the cellular genes coding for thymidine kinase, Wigler, M., et al., Cell 14: 725–731 (1978), hypoxanthine phosphoribosyltransferase, Willecke, K., et al., Molec. Gen. Genet. 170: 179–185 (1979), Graf, L. H., et al., Somat. Cell Genet., in press (1979), adenine phosphoribosyltransferase, Wigler, M., et al., Proc. Natl. Acad. Sci. USA, 76: 1373–1376 (1979), and dihydrofolate reductase, Wigler, M., et al., Proc. Natl. Acad. Sci., in press (1980); Lewis, W. H., et al., Somat. Cell. Genet., in press (1979). In this report is demonstrated the contransfer of the cloned Herpes simplex (HSV) thymidine kinase gene along with the human β-globin gene into mutant (tk⁻) teratocarcinoma stem cells in culture. These transformed cells, when tested by subcutaneous inoculation into mice, retain their developmental capacities in the tumors that are produced, and exhibit the viral-specific tk enzymatic activity for numerous cell generations in vivo.

TRANSFORMATION OF TK⁻ TERATOCARCINOMA CELLS

The addition of plasmid DNA containing the HSV thymidine kinase gene to cultures of attached mouse L tk⁻ cells yields L tk⁺ transformants in HAT at a frequency of one colony per 100 pg of DNA per $5 \times 10^5$ cells. Under identical transformation procedures, tk⁻ teratocarcinoma cells showed a strikingly lower transformation efficiency. Based on the average of three independent experiments, one surviving colony was obtained per 4 μg of plasmid DNA per $5 \times 10^5$ cells, a value four to five orders of magnitude below that of the L tk⁻ cells. This relatively low efficiency was confirmed when the DNA was added to TCC tk⁻ cells in suspension. Addition of 10 μg of Bam H1-restricted ptk-1 DNA to $7 \times 10^6$ cells resulted in only four transformants in HAT. With identical transformation conditions, L tk⁻ cells gave $3 \times 10^3$ tk⁺ colonies per $10^7$ cells per 1.5 μg of ptk-1 DNA. While high concentrations of gene are thus required to effect transformation in this teratocarcinoma cell line, the availability of cloned DNA nonetheless allows numerous tk⁺ transformants to be obtained.

EXPRESSION OF HSV TK ACTIVITY IN TRANSFORMED TERATOCARCINOMA CELLS

To ascertain whether the tk⁺ phenotypes of the TCC clones were indeed attributable to expression of the viral tk gene, seven colonies were picked from independent culture dishes and grown into mass cultures for testing. The activity of five clones were characterized by serological, and of two by biochemical, techniques. The Herpes-type antigenic identity of tk was verified by assaying the ability of HSV- tk-specific antibody to neutralize enzymatic activity. Over 90% inhibition of tk activity was in fact observed when immune serum was reacted with extracts of each of the five transformed clones chosen (Table I). The low residual activity remaining after neutralization of transformed-cell extracts may represent mitochondrial tk activity, which by itself is unable to afford survival in HAT. Cell extracts from the other two TCC tk⁺ clones chosen were tested for tk electrophoretic mobility because of the marked difference between the mouse and HSV tk enzymes. While the TCC tk⁻ control, as expected, shows no major peak of activity, the transformants have the HSV tk characteristic peak migrating with an $R_f$ of 0.45, as shown for one of the clones.

TABLE 1

Specific neutralization of Herpes thymidine kinase in transformants

| Cell line source of extract | Activity with preimmune serum Units × 10⁻³ per ml | Activity with antiserum Units × 10⁻³ per ml | % Residual activity |
|---|---|---|---|
| TCC wt* | 2.8 | 3.0 | 107.0 |
| TCC tk⁻** | 0.05 | 0.06 | 100.0 |
| LHB 2b≠ | 3.4 | 0.06 | 2.0 |
| TCC tk-1§ | 2.1 | 0.17 | 8.0 |
| TCC tk-3 | 5.5 | 0.43 | 8.0 |
| TCC tk-4 | 6.1 | 0.15 | 2.5 |
| TCC tk-5 | 3.7 | 0.21 | 6.0 |

30,000 × g supernatants of homogenates (S-30) from the indicated cell lines were mixed with preimmune serum or antiserum to purified HSV-1 tk, and tk activity was assayed as described in Materials and Method. Activity is expressed as units per ml of the S-30 fraction.
*TCC wt is a mouse teratocarcinoma feeder-independent cell line (6050P) with tk⁺ (wild-type) phenotype.
**TCC tk⁻ is a derivative of TCC wt that is resistant to BrdUrd and is tk-deficient.
≠LHB 2b is a mouse L tk⁻ cell line transformed to the tk⁺ phenotype with the Herpes thymidine kinase gene.
§TCC tk-1, -3, -4, and -5 are HAT-resistant teratocarcinoma clones derived from TCC tk⁻ after transformation with the Herpes thymidine kinase gene.

THE PHYSICAL STATE OF THE TK GENE IN TRANSFORMED TERATOCARCINOMA CELLS

The number of viral tk gene fragments and the location of these fragments in independent transformants were examined utilizing the blot hybridization technique of Southern, Southern, E. M., J. Mol. Biol., 98: 503–517 (1975). The donor DNA was the recombinant plasmid, ptk-1, digested to completion with Bam H1. This plasmid contains a 3.4 kb fragment with the viral tk gene inserted at the single Bam H1 site within the tetracycline resistance gene of pBR322. Transformation with Bam-cleaved tk DNA results in integration with loss of the Bam sites at the termini of the 3.4 kb fragment. High molecular weight DNA from transformants was cleaved with Bam H1, fractionated by agarose gel electrophoresis, and transferred to nitrocellulose filters; the filters were then annealed with nick-translated ³²P-tk DNA. In each cell clone, a single annealing fragment was seen; therefore, each clone contains at least one viral tk gene. As expected, each clone reveals a band of molecular weight greater than 3.4 kb. The molecular weights of the annealing fragments differ among the transformed clones, a result suggesting that integration has occurred at different sites within the DNA of the respective transformants.

STABILITY OF THE TRANSFORMED PHENOTYPE IN CULTURE

To test the capacity of the TCC transformants to retain expression of the donor tk gene in culture in the absence of selective pressure, individual clones grown into mass culture in HAT selective medium were subcultured for various periods in the absence of the selective agent. The fraction of cells that retained the tk+ phenotype was determined by measuring cloning efficiencies in selective and nonselective media. Wide differences among clones became apparent (Table II). Some cell lines,

TABLE II

In vitro stability of the transformed phenotype in teratocarcinoma cells.

| Clonal cell line | Experiment | Generations in nonselective medium* | Relative cloning efficiency in selective medium** | Rate of loss of tk+ phenotype per generation≠ |
|---|---|---|---|---|
| TCC tk-1 | 1 | 28 | 0.45 | |
| | 2 | 150 | 0.50 | <0.001 |
| TCC tk-2 | 1 | 28 | 0.23 | |
| | 2 | 150 | 0.02 | 0.017 |
| TCC tk-3 | 1 | 28 | 0.47 | |
| | 2 | 150 | 0.27 | 0.002 |
| TCC tk-4 | 1 | 28 | 0.26 | |
| | 2 | 150 | 0.16 | 0.003 |
| TCC tk-5 | 1 | 28 | 0.14 | |
| | 2 | 150 | 0.01 | 0.021 |

*Clones were picked and grown in HAT selective medium for 40 cell generations. Cells were then grown in nonselective medium for 28 or 150 generations prior to determining their cloning efficiencies under selective and nonselective conditions.
**One hundred cells were plated in triplicate into HAT selective and nonselective media. The relative cloning efficiency in selective medium is defined as the ratio of the cloning efficiency under selective conditions to the cloning efficiency under nonselective conditions (50–70%).
≠In these calculations it is assumed that for any given cell line the rate of loss of the tk phenotype is constant in each cell generation. The rate of loss per generation may then be calculated from the formula $F_M(1 - X)^{N-M} + F_N$, in which $F_M$ is the relative cloning efficiency in selective medium after M generations in non-selective medium; $F_N$ is similarly defined for N generations; and X is the rate of loss per cell generation. such as TCC tk-1, were relatively stable and lost the tk+ phenotype at frequencies less than 0.1% per generation in nonselective medium. Other, less stable, lines (TCC tk-2 and TCC tk-5) lost tk+ expression at 2% per generation in the absence of selection.

MAINTENANCE AND EXPRESSION OF THE HSV TK GENE IN VIVO DURING TISSUE DIFFERENTIATION IN TUMORS

The more critical question of retention of the foreign gene and of its expression during TCC cell differentiation in vivo in the absence of selection was examined in solid tumors. Tumors were formed by inoculating syngeneic hosts (usually two hosts per clone) subcutaneously with $10^7$ cells from each of the same five transformed clones. DNA from these tumors was analyzed by blot hybridization. Neutralization assays and electrophoretic mobility tests of the tk enzyme were also carried out to identify expression of the viral gene. In addition, samples of the same tumors were fixed and examined histologically for evidence of differentiation.

The restriction fragment profiles of the viral tk gene demonstrated that the gene was retained in all nine tumors analyzed. When each tumor (grown without HAT selection) was compared with its cell line of origin (cultured under HAT selective pressure), the number and location of the annealing fragments in seven of the tumors was identical to that of the corresponding cell line. Thus, the introduced tk gene was, in most cases, maintained for many cell generations spanning at least three weeks in vivo without significant loss or translocation. In two instances, however, a gene rearrangement had occurred, resulting from the loss of the original tk-containing fragment and the appearance of a new fragment of different molecular weight. It is of interest that these two tumors were produced from the two TCC clones that lost the tk+ phenotype in vitro at highest frequencies (Table II).

The results of neutralization tests with HSV-tk-specific antiserum demonstrated that at least three of the nine tumors (including one from the TCC tk-1 clone) had viral-type tk activity. (The presence of host cells in the tumors probably contributed substantial amounts of non-neutralized mouse tk in the remaining cases.) Another sample of the tumor derived from the TCC tk-1 line was also analyzed electrophoretically for HSV tk activity; a predominant peak migrating with an $R_f$ of 0.45, characteristic of the viral enzyme, was observed.

Histological speciments from each of the tumors were prepared and examined. In addition ot the TCC stem cells, tumors contained an array of differentiated tissues similar to those in tumors from the untransformed TCC wt and TCC tk− cell lines of origin. Included were muscle, neural formations, adipose tissue, some bone, squamous keratinizing epithelium, and other epithelia, ducts, and tubules.

COTRANSFORMATION OF TERATOCARCINOMA CELLS WITH THE HUMAN β-GLOBIN GENE

Biochemical transformants of mouse L may constitute a competent subpopulation in which an unselectable gene can be introduced, along with an unlinked selectable gene, at frequencies higher than in the general population, Wigler, M., et al., Cell 16: 777–785 (1979). Cotransformation experiments have therefore been carried out in which the Herpes viral tk gene was used as a selectable marker to introduce the human β-globin gene into tk− TCC cells. A cloned Hind III restriction endonuclease fragment of human chromosomal DNA containing the β-globin gene (plasmid phβ-8) was cleaved with the enzyme Hind III and mixed with Hind III-linearized ptk-1. After TCC tk− cells were exposed to these genes, they were grown for two weeks in HAT selection medium and tk+ transformants were cloned and analyzed by blot hybridization for presence of human β-globin sequences. A 4.3 kb Bgl II restriction fragment containing the intact human β-globin gene is entirely contained within the donor pH −8 plasmid. High molecular weight DNA from the transformants was therefore cleaved with the Bgl/32 II enzyme and analyzed in blot hybridization using the P-labeled 4.3 kb Bgl II fragment as an annealing probe.

In two of the ten TCC transformants examined, human β-globin sequences were detected. One of the transformants contains one to three copies of the 4.3 kb Bgl II fragment; in this cell line, therefore, the globin gene is evidently intact. The other TCC isolate containing the human β-globin gene displays an aberrant high moecular weight annealing fragment, a result suggesting that cleavage and integration have occurred within the Bgl II fragment. These data demonstrate that those TCC cells that are competent for uptake and expression of the tk gene also integrate another unlinked and unselectable gene at high frequency.

DISCUSSION

The experimental introduction of foreign DNA into early mammalian embryos, and its persistence and augmentation during development, were first reported some six years ago, Jaenisch, R. & Mintz, B., Proc. Natl. Acad. Sci. 71: 1250-1254 (1974). Purified (nonrecombinant) SV 40 viral DNA was microinjected into mouse blastocysts; they gave rise to healthy adults whose tissue DNA contained SV 40 gene sequences. Newer technologies such as described herein should allow a wide range of specific genes to be incorporated into the genome of the embryo for in vivo analyses of control of gene expression durring differentiation. With the advent of recombinant DNA, quantities of particular genes in native or specifically modified form can be obtained. In the biological sphere, the malignant stem cells of mouse teratocarcinomas have contributed a novel anenue of intervention. These cells can be grown in culture, selected for specific mutations, and microinjected into blastocysts, where they lose their neoplastic properties and participate in devlopment, Dewey, M., J. et al., Proc. Natl. Acad., Sci. USA, 74: 5564-5568 (1977); Watanabe, T., et al., Proc. Natl. Acad. Sci., 75: 5113-5117 (1978). The cultured TCC cells have therefore been viewed as vehicles for transmitting predetermined genetic changes to mice, Mintz, B., Brookhaven Symp., Bio., 29: 82-85, (1977); Mintz, B., Differentiation 13: 25-27 (1979). Such changes obviously might include genes acquired by uptake of DNA.

DNA-mediated gene transfer into cells of fibroblast lines has been accomplished in culture, Wigler, M., et al., Cell 11: 223-232 (1977); Wigler, M., et al., Cell 14: 725-731 (1978); Willecke, K., et al., Molec. Gen. Genet. 170: 179-185 (1979), Graf, L. H., et al., Somat. Cell Genet., in press (1979); Wigler, M., et al., Proc. Natl. Acad. Sci. USA, 76: 1373-1376 (1979); Wigler, M., et al. Proc. Natl. Acad. Sci., in press (1980); Lewis, W. H. et al., Somat. Cell Genet., in press (1979), and furnished the basis for similar attempts here with teratocarcinoma lines. The TCC-cell route for gene transfer into embryos, as compared with embryo injection of DNA, offers the advantage that transformants, i.e., cell clones in which the specific gene has been retained, can be identified and isolated by selection or screening. In the case of unselectable genes, cotransfer with a selectable one has been found to occur with relatively high frequency, Wigler, M., et al., Cell 16: 777-785 (1979).

In the present study, tk⁻ teratocarcinoma cells have been treated with the cloned thymidine kinase gene of *Herpes simplex* and a number of HAT-resistant tk+ clones have been obtained with a frequency of about one transformant per µg of DNA. The reason for the markedly lower frequency of TCC transformants than of L-cell transformants, Wigler, M., et al., Cell 14: 725-731 (1978), is obscure since the basis for transformation competence in eucaryotic cells remains unknown. The donor origin of the tk+ phenotype in the TCC transformants was demonstrated by the HSV-type electrophoretic mobility of their tk enzyme, and also by neutralization of the tk activity by specific antiserum raised against HSV-1 tk (Table I). Furthermore, blot hybridization tests indicated that at least one intact copy of the viral tk gene was present and integrated into other DNA in the transformed cells. These data support the conclusion that the tk activity in the transformed clones is indeed attributable to presence and expression of the viral gene.

A requirement for experiments involving the introduction of genes is that they remain stable in vivo, even in the absence of selective pressure, during many cell generations. Stability of the tk+ transformed phenotype was in fact not only in culture (Table II), but also in tumors arising after subcutaneous inoculation of the stem cells into mice. These tumors exhibited various types of tissue differentiation, similar to the range observed in the untransformed parent TCC line. Hybridization experiments comparing each tumor with its transformed cell line of origin indicated that the donor tk gene was maintained without significant loss or rearrangement in seven of nine tumors examined.

Many genes of interest in a developmental context are not selectable. An example is the globin gene. As in related experiments with L-cells, Wigler, M., et al., Cell 16: 777-785 (1979), a fragment of human genomic DNA containing an intact β-globin gene was administered to TCC tk⁻ cells along with the unlinked HSV tk gene. This proved to be an effective method to obtain TCC tk+ clones in which, from hybridization evidence, the human β-globin gene was present.

The experiments described herein therefore demonstrate that cultured TCC stem cells can accept exogenous genes and that such genes can be stably retained as well as expressed during in vivo differentiation in tumors. On this basis, experiments with a euploid TCC cell line can proceed, for the purpose of creating in vivo markers appropriate for analyses of gene regulation during embryogenesis.

MATERIALS AND METHODS

Cell Cultures

Ltk aprt, a derivative of Ltk clone D, Kit, S. et al., Esp. Cell Res. 31:291-312 (1963), was maintained in Dulbecco's modified Eagle's medium (DME) containing 10% calf serum (Flow Laboratories, Rockville, MD.) and 50 µg/ml of diaminopurine (DAP). Prior to transformation, cells were washed and grown for three generations in the absence of DAP. A Chinese hamster cell line containing an altered dihydrofolate reductase (rendering it resistant to methoxtrexate) A29 Mtx$^{RIII}$, Flintoff, W. F., et al, Somatic Cell Genetics 2:245-261 (1976), was propogated in DME supplemented with 3× non-essential amino acids, 10% calf serum and 1 µg/ml amethopterin. For the amplification experiments, the medium was additionally supplemented with 20 µg/ml of methotrexate.

Murine Ltk⁻aprt⁻cells are adenine phosphoribosyltransferase-negative derivaties of Ltk⁻clone D cells. Cells were maintained in growth medium and prepared for transformation as described, Wigler, M., et al., PNAS 76:1373-1376 (1979).

HEp-2(human), HeLa(human), CHO (Chinese hamster ovary), and Ltk⁻cells were gown in growth medium. LH2b, a derivative of Ltk⁻transformed with herpes simples virus tk DNA, was maintained in growth medium containing hypoxanthine at 15 µg/ml, aminopterin at 0.2 µg/ml, and thymidine at 5.0 µg/ml (HAT), Wigler, M., et al., Cell 1:223-232 (1977). All culture dishes were Nunclon (Vanguard International, Neptune, N.J.) plastic.

The feeder-independent mouse teratocarcinoma cell culture line 6050P, Watanabe, T., et al., PNAS 75:5113–5117 (1978), obtained from a tumor of the OTT 6050 transplant line, was used as the wild-type, or tk+, parent and is here designated TCC wt. This line is of the X/O sex chromosome type and has a modal number of 39 chromosomes with characteristics described in Watanabe, T., et al., (1978). The cells were grown in Dulbecco's modified Eagle's medium with 10% fetal calf serum. After 3 hr of exposure to 3 μg/ml of the mutagen N-methyl-N'-nitro-N-nitrosoguanidine, the cells were allowed to recover for two days and were then transferred to medium with 80 μg/ml of BrdUrd. A series of resistant clones were isolated; one supplied the clonal line (TCC tk−) used in the present transformation experiements. This line had a revision frequency to wild-type of less than $10^{-8}$. The cells were maintaned in medium with 30 μg/ml of BrdUrd and, prior to transformation, were washed and grown for three generations in the absence of the drug. Transformation efficiency was compared with that of a tk-deficient line, Kit, S., et al., Exp. Cell. Res. 31:297–312 (1963) of mouse L-cells (L tk−).

Extraction and Restriction Endonuclease Cleavage of Genomic DNA

High molecular weight DNA was obtained from cultured cells (CHO, LH2b, and HeLa) or from frozen rabbit livers as previously described. Wigler, M., et al., Cell 14:725–731 (1978). High molecular weight salmon sperm DNA was obtained from Worthington. Restriction endonuclease cleavage (Bam I, HindIII, Kpn I, and Xba I) was performed in a buffer containing 50 mM NaCl, 10 mM Tris.HCL, 5 mM $MgCl_2$, 7 mM mercaptoethanol, and bovine serum albumin at 100 μg/ml (pH 7.9). The enzyme-to-DNA ratio was at least two units/μg of DNA, and reaction mixtures were incubated at 37° C. for at least 2 hrs (one unit is the amount of enzyme that digests 1 μg of DNA in 1 hr). To monitor the completeness of digestion, 1 μl of nick-translated adenovirus-2 [$^{32}P$]DNA was incubated with 5 μl of reaction volume for at least 2 hr, cleavage products were separated by electrophoresis in 1% agarose gels, and digestion was monitored by exposing the dried gel to Cronex 2DC x-ray film.

Intact herpes simplex virus (HSV) DNA was isolated from CV-1-infected cells as previously described. Pellicer, A., et al., Cell 14:133–141 (1978). DNA was digested to comletion with Kpn I (New England Biolabs) in a buffer containing 6 mM Tris (pH 7.9), 6mM $MgCl_2$, 6 mM 2-mercaptoethanol, 6 mM NaCl and 200 μg/ml bovine serum albumin. The restricted DNA was fractionated by electrophoresis through 0.5% agarose gels (17×20×0.5 cm) for 24 hr at 70 V, and the 5.1 kb tk-containing fragment was extracted from the gel as described by Maxam, A. M. and Gilbert, W. PNAS 74:560–564 (1977) and Wigler, M., et al., Cell 14:725–731 (1978)

ΦX174 am3 RFI DNA was purchased ffrom Bethesda Research Laboratories. Plasmid pBR322 DNA was grown in E. coli HB 101 and purified according to the method of Clewell, D. B., J. Bacteriol. 110:667–676 (1972). The cloned rabbit β major globin gene in the λ Charon4A derivative (RβG-1) was identified and isolated as previously described. Maniatis, T., et al., Cell 15:687–701 (1978).

In the amplification experiments, the size of the high molecular weight DNA was determined by electrophoresis in 0.3% agarose gels using herpes simplex virus DNA and its Xba I fragments as markers. Only DNA whose average size was larger than 75 kb was found to possess transforming activity in the amplification experiments. In these experiments, plasmid DNAs were isolated from chloramphenicol amplified cultures by isopycnic centrifugation in CsCl gradients containing 300 μg/ml ethidium bromide.

TRANSFORMATION AND SELECTION

The transformation protocol was as described in Graham, F. L. and Van der Eb, A. J., Virology, 52:456–457 (1973) with the following modifications. One day prior to transformation, cells were seeded at $0.7 \times 10^6$ cells per dish. The medium was changed 4 hr prior to transformation. Sterile, ethanol-precipitated high molecular weight or restriction endonuclease-cleaved eucaryotic DNA dissolved in 1 mM Tris (pH 7.9)/0.1 mM EDTA was used to prepare DNA/$CaCl_2$ which contains DNA at 40 μg/ml and 250 mM $CaCl_2$ (Mallinkrodt). Twice-concentrated Hepes-buffered saline (2× HBS) was prepared; it contains 280 mM NaCl, 50 mM Hepes, and 1.5 mM sodium phosphate, pH adjusted to 7.10±0.05. DNA/$CaCl_2$ solution was added dropwise to an equal volume of sterile 2× HBS. A 1-ml sterile plastic pipette with a cotton plug was inserted into the mixing tube containing 2× HBS, and bubbles were introduced by blowing while the DNA was being added. The calcium phosphate/DNA precipitate was allowed to form without agitation for 30–45 min at room temperature. The precipitate was then mixed by gentle pipetting with a plastic pipette, and 1 ml of precipitate was added per plate, directly to the 10 ml of growth medium that covered the recipient cells. After 4-hr incubation at 37° C., the medium was replaced and the cells were allowed to incubate for an additional 20 hr. At that time, selective pressure was applied. For tk+ selection, medium was changed to growth medium containing HAT. For aprt+ selection, cells were trypsinized and replated at lower density (about $0.5 \times 10^6$ cells per 10-cm dish) in medium containing 0.05 mM azaserine and 0.1 mM adenine. For both tk+ and aprt+ selection, selective media were changed the next day, 2 days after that, and subsequently every 3 days for 2–3 weeks while transformant clones arose. Colonies were picked by using cloning cylinders and the remainder of the colonies were scored after formaldehyde fixation and staining with Giemsa. For characterization, clones were grown into mass culture under continued selective pressure. A record was kept of the apparent number of cell doublings for each clone isolated.

Methotrexate-resistant transformants of Ltk− aprt− cells were obtained following transformation with 20 μg of high molecular weight DNA from A29 Mtx$^{RIII}$ cells and selection in DME containing 10% calf serum and 0.2 μg/ml amethopterin.

For tk+ selection, cells were grown in HAT medium, for resistance to methotrexate, cells were selected in medium supplemented with 0.1 μg/ml of methotrexate. Colonies were cloned from individual dishes to assure that each transformant arose from an independent event. Ligates between A29 and linearized pBR322 DNA were prepared by incubating a 1:1 ration (w/w) of Sal I-cleaved DNAs with T4 ligase (Bethesda Research Laboratories) under the conditions recommended by the supplier. A calcium phosphate precipitate was prepared using 2 μg ligate and 18 μg carrier/ml, and added to recipient cells (the amount of ligate was limited because of the observation that plasmid inhibits transformation). The DNA was allowed to remain in contact with the cells for 4-12 hr and the medium was then aspirated and replaced with fresh DME. Selective pressure was applied 24 hr following exposure to DNA. After 2-3 weeks, colonies were isolated using cloning cylinders.

In the mouse teratocarcinoma cell experiments, transformation was performed as described previously except that the TCC tk$^-$ cells were seeded at $3\times10^5$ cells/plate one day prior to transformation. To each plate of attached cells was added a calcium phosphate/DNA precipitate prepared with 4 μg of the recombinant plasmid, Ptk-1, digested with Bam H1, in the presence of 20 μg of high molecular weight DNA obtained from L tk$^-$ aprt$^-$ cells.

In addition, some cells were treated in suspension, Willecke, K. et al., Molec. Gen. Genet. 170:179-185 (1979). $7\times10^6$ freshly trypsinized TCC tk$^-$ cells were mixed with a calcium phosphate/DNA precipitate prepared with 10 μg of DNA from the BAM H1-claved plasmid Ptk-1 and 150 μg of high molecular weight DNA from salmon sperm. Following centrifugation, resuspension, and shaking, as described in Willecke, K. et al. (1979), the cells were again plated in growth medium. After three days, the medium was replaced with HAT medium and colonies of transformants were isolated after two weeks.

Cotransformation experiments were performed with 4 μg of Bam H1-digested Ptk-1 DNA along with 4 μg of Hind III-cleaved plasmid pHβ-8 containing the chromosomal adult human β-globin gene, Lawn, R. M., et al., Cell 15:1157-1174 (1978). Tk$^+$ transformants were selected in growth medium containing 0.1 mM hypoxanthine/0.4 μM aminopterin/16 μM thymidine(HAT). Colonies were picked with cloning cylinders and were grown into mass cultures.

COTRANSFORMATION OF DEFINED DNA SEQUENCES AND THE HSV TK GENE

Ltk$^-$ aprt$^-$ mouse cells were transformed with either 1-10 μg of ΦX174, 1 μg of pBR322 or 1 μg of RβG-1 DNA in the presence of 1 ng of HSV-1 tk gene and 10-20 μg of salmon sperm carrier DNA, as previously described. Wigler, M. et al., PNAS 76:1373-1376 (1979). Tk$^+$ transformants were selected in DME containing hypoxanthine, aminopterin and thymidine (HAT) and 10% calf serum. Isolated colonies were picked using cloning cylinders and grown into mass cultures.

ENZYME ASSAYS

Extracts were prepared by resuspending washed cell pellets (approximately $10^7$ cells) in 0.1 ml of 0.02 M potassium phosphate, pH 7, containing 0.5% Triton X-100. The supernatant (cytoplasm) obtained after 25 min of 700×g centrifugation was used for the quantitation of enzymatic activity and for electrophoresis. aprt and protein were assayed as previously described. Chasin L. A., Cell 2:37-41 (1974). Inclusion of 3 mM thymidine triphosphate, an inhibitor of 5'-nucleotidase, Murray, A. W. and Friedrichs, B., Biochem., J. 111:83-89 (1969), in the reaction mixture did not increase AMP recovery, indicating that the nucleotidase was not interfering with the measurement of aprt activity. Isoelectric focusing of aprt was carried out essentially as described for hypoxanthine phosphoribosyltransferase, Chasin, L. A. and Urlaub, G. Somat. Cell Genet. 2:453-467 (1976), with the following exceptions: The polyacrylamide gel contained an Ampholine (LKB) mixture of 0.8% pH 2.5-4, 0.8% pH 4-6, and 0.4% pH 5-7. For assaying enzymatic activity, [2-$^3$H] adenine [0.04 mM, 1 Ci/mmol, New England Nuclear (1 Ci=$3.7\times10^{10}$ becquerels)] was substituted for hypoxanthine.

ASSAYS OF THYMIDINE KINASE ACTIVITY

For specific activity measurements, cells from monolayer cultures were scraped into phosphate buffered saline and washed. The cell pellet was suspended in 5 volumes of extraction buffer (0.01 M Tris.HCl, pH 7.5, 0.01 M KCl, 1mMMgCl$_2$, 1mM 2-mercaptoethanol, and 50 μM thymidine). The cell suspension was frozen and thawed three times and the KCl concentration was then adjusted to 0.15 M. After sonication, the cytoplasmic extract was obtained by centrifugation at 30,000×g for 30 min, and the supernatant was used for tk assays as described in Wigler, M. et al. Cell 16:777-785 (1979). Cytoplasmic extracts from tumors were obtained after disruption of the cells in a Potter-Elvejehm homogenizer. They were then treated as described above for cultured cells. One unit of thymidine kinase is defined as the amount of enzyme which converts one nanomole of thymidine into thymidine monophosphate per minute.

In enzyme neutralization studies, anti-HSV-1 tk antiserum or preimmune serum was mixed with an equal volume of cytoplasmic extract, and ATP and magnesium were added to 6.7 mM. The enzyme-antibody mixture was incubated for 30 min at room temperature, centrifuged at 2,000×g for 10 min, and the supernatant was assayed for tk activity.

In an additional biochemical assay, 30,000×g supernatants of homogenates from cell cultures and from solid tumors were electrophoresed on 5% polyacrylamide gels which were then cut into 1.6 mm slices and assayed for tk activity as described. Lee, L. S. and Cheng, Y. C., J. Biol. Chem., 251:2600-2604 (1976).

RNA Isolation

Total RNA was isolated from logarithmic-phase cultures of transformed L cells by successive extractions with phenol at pH 5.1, phenol/chloroform/isoamyl alcohol (25:24:1, vol/vol), and chloroform/isoamyl alcohol (24:1, vol/vol). After ethanol precipitation, the RNA was digested with DNase, Maxwell, I. H., et al., Nucleic Acids Res. 4:241-246 (1977) and precipitated with ethanol. Nuclear and cytoplasmic fractions were isolated as described in Wigler, M. et al., PNAS 76:1373-1376 (1979) and RNAs were extracted as described above. Cytoplasmic polyadenylylated RNA was isolated by oligo(dT)-cellulose chromatography. Axel, R. et al., Cell 7:247-254 (1976).

CDNA SYNTHESIS

Rabbit and mouse cDNAs were prepared by using avian myeloblastosis virus reverse transcriptase (RNA-dependent DNA polymerase) as described in Myers, J. C. and Spiegelman, S., PNAS 75:5329-5333 (1978).

ISOLATION OF TRANSFORMED CELL DNA

Cells were harvested by scraping into PBS and centrifuging at 1000×g for 10 min. The pellet was resuspended in 40 vol of TNE [10 mM Tris-HCl (ph 8.0), 150 mM NaCl, 10 mM EDTA], and SDS and proteinase K were added to 0.2% and 100 μg/ml, respectively. The lysate was incubated at 37° C. for 5-10 hr and then extracted sequentially with buffer-saturated phenol and CHCl$_3$. High molecular weight DNA isolated by mixing the aqueous phase with 2 vol of cold ethanol and immediately removing the precipitate that formed. The DNA was washed with 70% ethanol and dissolved in 1 mM Tris, 0.1 EDTA.

Nuclei and cytoplasm from clones ΦX4 and ΦX5 were prepared as described by Ringold, G. M., et al. Cell 10:19–26 (1977). The nuclear fraction was further fractionated into high and low molecular weight DNA as described by Hirt, B., J. Mol. Biol. 26:365–369 (1967).

DNA FILTER HYBRIDIZATIONS

Cellular DNA was digested with restriction endonucleases, electrophoresed on agarose slab gels, transferred to nitrocellulose filter sheets, and hybridized with $^{32}$P-labeled DNA probes as described by Wigler, M. et al., PNAS 76:1373–1376 (1979).

DNA from transformed cells was digested with various restriction endonucleases using the conditions specified by the supplier New England Biolabs or Bethesda Research Laboratories). Digestions were performed at an enzyme to DNA ratio of 1.5 U/μg for 2 hr at 37° C. Reactions were terminated by the addition of EDTA, and the product was electrophoresed on horizontal agarose slab gels in 36 mM Tris, 30 mM NaH$_2$PO$_4$, 1 mM EDTA (pH 7.7). DNA fragments were transferred to nitrocellulose sheets, hybridized and washed as previously described. Weinstock, R., et al., PNAS 75:1299–1303 (1978) with two modifications. Two nitrocellulose filters were used during transfer. Jeffreys, A. J. and Flavell, R. A., Cell 12:1097–1108 (1977). The lower filter was discarded, and following hybridization the filter was washed 4 times for 20 min in 2×SSC, 25 mM sodium phosphate, 1.5 mM Na$_4$P$_2$O$_7$, 0.05% SDS at 65° C. and then successively in 1:1 and 1:5 dilutions of this buffer. Jeffreys, A. J. and Flavell, R. A., Cell 12:429–439 (1977).

In the amplification experiments the probes were either $^{32}$P-nick translated pBR322 or pdhfr-21, a cDNA copy of mouse dhfr mRNA. Chang, A.C.Y., et al., Nature 275:617–624 (1978).

SOLUTION HYBRIDIZATIONS $^{32}$P-Labeled globin cDNAs (specific activities of 2–9×10$^8$ cpm/μg) were hybridized with excess RNA in 0.4 M NaCl/25 mM 1,4-piperazinediethanesulfonic acid (Pipes), pH 6.5/5 mM EDTA at 75° C. Incubation times did not exceed 70 hr. R$_0$ts were calculated as moles of RNA nucleotides per liter times time in seconds. The fraction of cDNA rendered resistant to the single-strand nuclease S1 in hybridization was determined as described. Axel, R. et al., Cell 7:247–254 (1976).

RNA FILTER HYBRIDIZATION

RNA was electrophoresed through 1% agarose slab gels (17×20×0.4 cm) containing 5 mM methylmercury hydroxide as described by Bailey, J. and Davidson, N., Anal. Biochem. 70:75–85 (1976). The concentration of RNA in each slot was 0.5 μg/μl. Electrophoresis was at 110 V for 12 hr at room temperature.

RNA was transferred from the gel to diazotized cellulose paper as described by Alwine, J. C., et al., PNAS 74:5350–5354 (1979) by using pH 4.0 citrate transfer buffer. After transfer, the RNA filter was incubated for 1 hr with transfer buffer containing carrier RNA at 500 μg/ml. The RNA on the filters was hybridized with cloned DNA probe at 50 ng/ml labeled by $^{32}$P-nick translation, Weinstock, R., et al., PNAS 75:1299–1303 (1978) to specific activities of 2–8×10$^8$ cpm/μg. Reaction volumes were 25 μl/cm$^2$ of filter. Hybridization was in 4× standard saline citrate (0.15 M NaCl/0.015 M sodium citrate)/50% formamide at 57° C. for 36–48 hr.

After hybridization, filters were soaked in two changes of 2× standard saline citrate/25 mM sodium phosphate/1.5 mM sodium pyrophosphate/0.1% sodium dodecyl sulfate/5 mM EDTA at 37° C. for 30 min with shaking to remove formamide. Successive washes were at 68° C. with 1× and 0.1× standard saline citrate containing 5 mM EDTA and 0.1% sodium dodecyl sulfate for 30 min each.

BERK SHARP ANALYSIS OF RABBIT β-GLOBIN RNA IN TRANSFORMED MOUSE L CELLS

The hybridizations were carried out in 80% (vol/vol) formamide (Eastman)/0.4 M Pipes, pH 6.5/0.1 mM EDTA/0.4 M NaCl, Casey, J. and Davidson, N., Nucleic Acid Res., 4:1539–1552 (1977); Berk, A. J. and Sharp, P. A., Cell 12:721–732 (1977) for 18 hr at 51° C. for the 1.8 kbp Hha I fragment and 49° C. for the Pst 1 fragment. The hybrids were treated with S1 nuclease and analyzed essentially by the procedure described by Berk, A. J. and Sharp, P. A. (1977).

Although the instant disclosure sets forth all essential information in connection with the invention, the numerous publications cited herein may be of assistance in understanding the background of the invention and the state of the art. Accordingly, all of the publications cited are hereby incorporated by reference into the present disclosure.

What is claimed is:

1. A process for inserting foreign DNA I into a suitable eucaryotic cell which comprises cotransforming said eucaryotic cell with said foreign DNA I and with unlinked foreign DNA II which codes for a selectable phenotype not expressed by said ducaryotic cell, said cotransformation being carried out under suitable conditions permitting survival or identification of eucaryotic cells which have acquired said selectable phenotype, said foreign DNA I being incorporated into the chromosomal DNA of said eucaryotic cell.

2. A process in accordance with claim 1 wherein said foreign DNA I codes for proteinaceous material which is not associated with a selectable phenotype.

3. A process in accordance with claim 2 wherein said foreign DNA I codes for interferon protein.

4. A process in accordance with claim 2 wherein said foreign DNA I codes for insulin.

5. A process in accordance with claim 2 wherein said foreign DNA I codes for growth hormone.

6. A process in accordance with claim 2 wherein said foreign DNA I codes for a clotting factor.

7. A process in accordance with claim 2 wherein said foreign DNA I codes for a viral antigen or an antibody.

8. A process in accordance with claim 2 wherein said foreign DNA I codes for an enzyme.

9. A process in accordance with claim 1 wherein said foreign DNA I is substantially purified.

10. A process in accordance with claim 1 wherein said foreign DNA I has been obtained from restriction endonuclease cleavage of eucaryotic chromosomal DNA.

11. A process in accordance with claim 1 wherein said foreign DNA I and DNA II have been treated with calcium phosphate.

12. A process in accordance with claim 1 wherein said eucaryotic cell is a mammalian cell.

13. A process in accordance with claim 12 wherein said mammalian cell is an erythroblast.

14. A process in accordance with claim 12 wherein said mammalian cell is a fibroblast.

15. A process in accordance with claim 1 wherein said foreign DNA I is present in an amount relative to said DNA II which codes for a selectable phenotype in the range from about 1:1 to about 100,000:1.

16. A process in accordance with claim 1 wherein said DNA II which codes for a selectable phenotype comprises the gene for thymidine kinase from herpes simplex virus.

17. A process in accordance with claim 1 wherein said DNA II which codes for proteinaceous material which is associated with a selectable phenotype comprises the gene for adenine phosphoribosyltransferase.

18. A process in accordance with claim 1 wherein said DNA II which codes for a selectable phenotype comprises a gene associated with drug resistance.

19. A process in accordance with claim 18 wherein said gene associated with drug resistance is the gene coding for a mutant dihydrofolate reductase which renders cells resistant to methotrexate.

20. A eucaryotic cell into which foreign DNA I has been inserted in accordance with the process of claim 1.

21. A mammalian cell into which foreign DNA I has been inserted in accordance with the process of claim 1.

22. A process for producing a foreign proteinaceous material which comprises cotransforming a eucaryotic cell in accordance with the process of claim 1, culturing or cloning said cotransformed eucaryotic cell under suitable conditions to yield a multiplicity of eucaryotic cells producing said foreign proteinaceous material and recovering said proteinaceous material from said eucaryotic cells.

23. A process in accordance with claim 22 wherein said proteinaceous material comprises interferon protein, insulin, growth hormone, clotting factor, viral antigen or antibody.

24. A process in accordance with claim 22 wherein said eucaryotic cell is a mammalian cell.

25. A method of detecting eucaryotic cells which have been transformed with foreign DNA I which is not associated with a selectable phenotype which comprises cotransforming said eucaryotic cell with said DNA I and with DNA II which is associated with a selectable phenotype in accordance with the process of claim 1, and screening for eucaryotic cells so cotransformed.

26. A process for inserting foreign DNA I into a eucaryotic cell which comprises cotransforming said eucaryotic cell with said foreign DNA I and with unlinked foreign DNA II which codes for a selectable phenotype not expressed by said eucaryotic cell, said cotransformation being carried out in a suitable medium and in the presence of conditions permitting identification and recovery of eucaryotic cells which have acquired said selectable phenotype.

27. A process for cotransforming a suitable eucaryotic cell which comprises transforming under suitable conditions said eucaryotic cell with foreign DNA I and with foreign DNA II, said DNA I and DNA II being unlinked and said DNA II coding for a selectable phenotype not expressed by said eucaryotic cell prior to cotransformation.

28. A process for inserting purified foreign DNA I coding for proteinaceous material which is not associated with a selectable phenotype into a suitable eucaryotic cell which comprises cotransforming said eucaryotic cell with said foreign DNA I and with unlinked foreign DNA II coding for proteinaceous material which is associated with a selectable phenotype, said cotransformation being carried out under suitable conditions permitting survival or identification of eucaryotic cells which have acquired said selectable phenotype, said foreign DNA I being incorporated into the chromosomal DNA of said eucaryotic cell.

29. A process in accordance with claim 28 wherein said proteinaceous material which is not associated with a selectable phenotype comprises interferon protein, insulin, growth hormone, clotting factor, viral antigen or antibody.

30. A eucaryotic cell into which foreign DNA I has been inserted in accordance with the process of claim 28.

31. A process for inserting a multiplicity of foreign DNA I molecules corresponding to multiple copies of a gene coding for a proteinaceous material into a suitable eucaryotic cell which comprises cotransforming said eucaryotic cell with said multiplicity of foreign DNA I molecules and with a multiplicity of unlinked foreign DNA II molecules coding for a selectable phenotype not expressed by said eucaryotic cell, said cotransformation being carried out under suitable conditions permitting survival or identification of eucaryotic cells which have acquired said multiplicity of genes coding for said selectable phenotype.

32. A process in accordance with claim 31 wherein said foreign DNA I codes for proteinaceous material which is not associated with a selectable phenotype.

33. A process in accordance with claim 32 wherein said foreign DNA I codes for interferon protein.

34. A process in accordance with claim 32 wherein said foreign DNA I codes for insulin.

35. A process in accordance with claim 32 wherein said foreign DNA I codes for growth hormone.

36. A process in accordance with claim 32 wherein said foreign DNA I codes for a clotting factor.

37. A process in accordance with claim 32 wherein said foreign DNA I codes for a viral antigen or an antibody.

38. A process in accordance with claim 32 wherein said foreign DNA I codes for an enzyme.

39. A process in accordance with claim 31 wherein said foreign DNA I is substantially purified.

40. A process in accordance with claim 31 wherein said foreign DNA I has been obtained from restriction endonuclease cleavage of eucaryotic chromosomal DNA.

41. A process in accordance with claim 31 wherein said foreign DNA I and DNA II have been treated with calcium phosphate.

42. A process in accordance with claim 31 wherein said eucaryotic cell is a mammalian cell.

43. A process in accordance with claim 42 wherein said mammalian cell is an erythroblast.

44. A process in accordance with claim 42 wherein said mammalian cell is a fibroblast.

45. A process in accordance with claim 31 wherein said foreign DNA I is present in an amount relative to said DNA II which codes for proteinaceous material associated with a selectable phenotype in the range from about 1:1 to about 100,000:1.

46. A process in accordance with claim 31 wherein said foreign DNA II which does for proteinaceous material which is associated with a selectable phenotype comprises a gene associated with drug resistance.

47. A process in accordance with claim 46 wherein said gene associated with drug resistance is a gene coding for a mutant dihydrofolate reductase which renders cells resistant to methotrexate.

48. A process in accordance with claim 31 wherein said foreign DNA I is incorporated into the chromosomal DNA of said eucaryotic cell.

49. A eucaryotic cell into which foreign DNA I has been inserted in accordance with the process of claim 31.

50. A mammalian cell into which foreign DNA I has been inserted in accordance with the process of claim 31.

51. A process for producing a foregin proteinaceous material which comprises cotransforming a eucaryotic cell in accordance with the process of claim 31, maintaining said cotransformed eucaryotic cell under suitable conditions to produce said foreign proteinaceous material, and recovering said proteinaceous material so produced.

52. A process in accordance with claim 51 wherein said proteinaceous material comprises interferon protein, insulin, growth hormone, clotting factor, viral antigen or antibody.

53. A process in accordance with claim 51 wherein said eucaryotic cell is mammalian cell.

54. A process for generating a multiplicity of foregin DNA I molecules corresponding to multiple copies of a gene in a eucaryotic cell which comprises tranforming said eucaryotic cell with a molecule which is formed by linking one of said foreign DNA I molecules to a DNA II molecule corresponding to an amplifiable gene for a dominant selectable phenotype not expressed by said eucaryotic cell, and culturing the transformed eucaryotic cells in the presence of successively elevated concentrations of an agent permitting survival or identification of eucaryotic cells which have acquired multiple copies of said amplifiable gene, said transformation and culturing being carried out under suitable conditions.

55. A process in accordance with claim 54 wherein said foreign DNA I codes for proteinaceous material which is not associated with a selectable phenotype.

56. A process in accordance with claim 55 wherein said foreign DNA I codes for interferon protein.

57. A process in accordance with claim 55 wherein said foreign DNA I codes for insulin.

58. A process in accordance with claim 55 wherein said foreign DNA I codes for growth hormone.

59. A process in accordance with claim 55 wherein said foreign DNA I codes for a clotting factor.

60. A process in accordance with claim 55 wherein said foreign DNA I codes for a viral antigen or antibody.

61. A process in accordance with claim 55 wherein said foregin DNA I codes for an enzyme.

62. A process in accordance with claim 54 wherein said foreign DNA I is substantially purified.

63. A process in accordance with claim 54 wherein said foreign DNA I has been obtained from restriction endonuclease cleavage of eucaryotic chromosomal DNA.

64. A process in accordance with claim 54 wherein said foreign DNA I and DNA II have been treated with calcium phosphate.

65. A process in accordance with claim 54 wherein said eucaryotic cell is mammalian cell.

66. A process in accordance with claim 65 wherein said mammalian cell is an erythroblast.

67. A process in accordance with claim 65 wherein said mammalian cell is a fibroblast.

68. A process in accordance with claim 54 wherein said foreign DNA I is present in an amount relative to said DNA II which codes for proteinaceous material associated with a selectable phenotype in the range from about 1:1 to about 100,000:1.

69. A process in accordance with claim 54 wherein said DNA II which codes for proteinaceous material which is associated with a selectable phenotype comprises a gene associated with resistance to a drug or chemical antagonist.

70. A process in accordance with claim 69 wherein said gene associated with resistance to a drug or chemical anatgonist is a gene coding for a mutant dihydrofolate reductase which renders cells resistant to methotrexate.

71. A process in accordance with claim 54 wherein said foreign DNA I is incorporated into the chromosomal DNA of said eucaryotic cell.

72. A eucaryotic cell into which foreign DNA I has been inserted in accordance with the process of claim 54.

73. A mammalian cell into which foreign DNA I has been inserted in accordance with the process of claim 54.

* * * * *

UNITED STATES PATENT AND TRADEMARK OFFICE
CERTIFICATE OF CORRECTION

PATENT NO. : 4,399,216

DATED : August 16, 1983

INVENTOR(S) : Richard Axel, Michael H. Wigler, Saul J. Silverstein

It is certified that error appears in the above-identified patent and that said Letters Patent is hereby corrected as shown below:

Col. 3, line 35, after "hormones" insert a comma --(,)--.

Col. 8, line 51, after "pBR" insert --322--.

Col. 10, line 26, after "$\Phi$" insert --X--.

Col. 12, line 60, "transforments" should read --transformants--.

Col. 15, line 21, "ribbit" should read --rabbit--.

Col. 17, line 68, "therefor" should read --therefore--.

Col. 18, line 58, "exceding" should read --exceeding--.

Col. 22, line 20, "$tk^{30}$" should read --$tk^{+}$--.

Col. 23, line 57, "=P" should read --$^{32}P$--.

Col. 30, line 15, "$\mu$/ml" should read --$\mu g$/ml--.

Col. 30, line 52, "$\mu$/ml" should read --$\mu g$/ml--.

Col. 34, line 57, "Bgl/32" should read --Bgl--.

Col. 34, line 59, "P-labeled" should read --$^{32}P$-labeled--.

Col. 35, line 21, "anenue" should read --avenue--.

UNITED STATES PATENT AND TRADEMARK OFFICE
CERTIFICATE OF CORRECTION

PATENT NO. : 4,399,216                                    Page 2 of 2
DATED       : August 16, 1983
INVENTOR(S) : Richard Axel, Michael H. Wigler,
              Saul J. Silverstein It is certified that error appears in the above-identified patent and that said Letters Patent is hereby corrected as shown below:

Col. 37, line 57, "ffrom" should read --from--.

Col. 38, line 60, after "A29" insert --DNA--.

Col. 44, line 68, "does" should read --codes--.

Signed and Sealed this

Twenty-sixth Day of March 1985

[SEAL]

Attest:

DONALD J. QUIGG

Attesting Officer    Acting Commissioner of Patents and Trademarks